United States Patent
Wu et al.

(10) Patent No.: US 8,637,506 B2
(45) Date of Patent: Jan. 28, 2014

(54) COMPOSITIONS AND METHODS FOR BONE FORMATION AND REMODELING

(75) Inventors: Dianqing Wu, Chesire, CT (US); Yazhou Zhang, Farmington, CT (US); Peng Liu, West Hartford, CT (US); Xiaofeng Li, West Hartford, CT (US); Jie Zhang, Memphis, TN (US); Jufang Shan, Memphis, TN (US); Dean Engelhardt, New York, NY (US)

(73) Assignees: Enzo Biochem, Inc., Farmingdale, NY (US); University of Connecticut, Farmington, CT (US); St. Jude's Childrens Hospital, Memphis, TN (US)

( * ) Notice: Subject to any disclaimer, the term of this patent is extended or adjusted under 35 U.S.C. 154(b) by 391 days.

(21) Appl. No.: 10/849,067

(22) Filed: May 19, 2004

(65) Prior Publication Data

US 2005/0196349 A1   Sep. 8, 2005
US 2006/0198791 A2   Sep. 7, 2006

Related U.S. Application Data

(60) Provisional application No. 60/504,860, filed on Sep. 22, 2003.

(51) Int. Cl.
*A61K 31/535*   (2006.01)
*C07C 50/18*   (2006.01)

(52) U.S. Cl.
USPC ........................ 514/229.8; 552/208

(58) Field of Classification Search
None
See application file for complete search history.

(56) References Cited

U.S. PATENT DOCUMENTS

| | | | |
|---|---|---|---|
| 6,844,422 B1* | 1/2005 | Niehrs et al. | 530/350 |
| 2003/0138848 A1 | 7/2003 | Moarefi et al. | |
| 2003/0165500 A1* | 9/2003 | Rhee et al. | 424/143.1 |
| 2003/0181660 A1 | 9/2003 | Todd et al. | |
| 2004/0009535 A1 | 1/2004 | Brunkow | |
| 2004/0023356 A1 | 2/2004 | Krumlauf | |
| 2004/0038860 A1* | 2/2004 | Allen et al. | 514/2 |
| 2004/0235728 A1 | 11/2004 | Stoch | |
| 2005/0084494 A1 | 4/2005 | Prockop | |
| 2005/0196349 A1 | 9/2005 | Wu et al. | |
| 2005/0261181 A1 | 11/2005 | Wu et al. | |
| 2006/0030523 A1 | 2/2006 | Wu et al. | |
| 2006/0127393 A1 | 6/2006 | Li et al. | |
| 2006/0257892 A1 | 11/2006 | Cohen et al. | |
| 2008/0119402 A1 | 5/2008 | Zheng et al. | |
| 2010/0298308 A1 | 11/2010 | Wu et al. | |
| 2011/0105606 A1* | 5/2011 | Rabbani et al. | 514/533 |

FOREIGN PATENT DOCUMENTS

WO   WO 02/092015   11/2002
WO   WO 03/106657   12/2003

OTHER PUBLICATIONS

Boyden et al., N. Engl J Med. May 16, 2002;346(20):1513-21).*
Gallagher, 1990, .Metabolism, vol. 39, Issue 4, Supplement 1, Apr. 1990, pp. 27-29, Abstract only.*
Delise et al., Osteoarthritis Cartilage. Sep. 2000;8(5):309-334.*
Grotewold et al., (Int. J. Dev. Biol. 46: 943-947 (2002)).*
Day et al., Dev. Cell vol. 8, Issue 5, May 2005, pp. 739-750.*
Kim et al., (Cell, vol. 130, Issue 3, Aug. 10, 2007, pp. 470-483.*
DTP Datawarehouse Index Results, from http://dtp.nci.nih.gov/dtpstandard/servlet/dwindex?searchtype=NSC&outnutformat=html&searchlist=366218 accessed Dec. 3, 2007.
NCI Communication re InVivo screening: email From: Daniel Zaharevitz[zaharevitz@dtpax2.ncicrf.gov], Sent: Tuesday, Dec. 4, 2007 5:37 PM, to: Gamett, Daniel C., Subject: Re: In vivo screen data, p. 1 of 1.
NCI In Vivo Screening Data http://dtp.nci.nih.gov/dtpstandard/servlet/Invivoscreen?testshortname=tumor+PS . . . Accessed Dec. 3, 2007.
2001 NIH Consensus Conference Development Panel on Osteoporosis Prevention, Diagnosis and Therapy. JAMA 285:785-795.
Axford, John S. Glycobiology & Medicine: A Millenial Review, Jul. 11-12 2000 lecture at 5th Jenner Symposium held at Royal Society of Medicine, London, UK, http://www/glycoscience.com/glycoscience/document_viewer.wm?FILENAME=D006.
Babij et al., 2003, J Bone Miner Res 18:960-74.
Bafico et al., 2001, Nat Cell Biol 3:683-6.
Bain et al., 2003, Biochem Biophys Res Commun 301:84-91.
Barrandon, Yann Mar. 20, 2003, Nature vol. 422:272-273.
Boyden et al., May 16, 2002, N. Engl J Med 346(20):1513-21.
Capelluto et al. 2002, Nature 419(6908):726-9.

(Continued)

*Primary Examiner* — Daniel C Gamett
(74) *Attorney, Agent, or Firm* — Anna D. DiGabriele Petti, Esq.

(57) ABSTRACT

The mechanism by which the high bone mass (HBM) mutation (G171V) of the Wnt coreceptor LRP5 regulates the canonical Wnt signaling was investigated. The mutation was previously shown to reduce Dkk protein-1-mediated antagonism, suggesting that the first YWTD repeat domain where G171 is located may be responsible for Dkk protein-mediated antagonism. However, we found that the third YWTD repeat, but not the first repeat domain, is required for DKK1-mediated antagonism. Instead, we found that the G171V mutation disrupted the interaction of LRP5 with Mesd, a chaperon protein for LRP5/6 that is required for the coreceptors' transport to cell surfaces, resulting in less LRP5 molecules on the cell surface. Although the reduction in the level of cell surface LRP5 molecules led to a reduction in Wnt signaling in a paracrine paradigm, the mutation did not appear to affect the activity of coexpressed Wnt in an autocrine paradigm. Together with the observation that osteoblast cells produce autocrine canonical Wnt, Wnt7b, and that osteocytes produce paracrine Dkk1, we believe that the G171V mutation may cause an increase in Wnt activity in osteoblasts by reducing the number of targets for paracrine Dkk1 to antagonize without affecting the activity of autocrine Wnt.

3 Claims, 16 Drawing Sheets

(56) References Cited

OTHER PUBLICATIONS

Cheyette et al. 2002, Dev Cell, vol. 2, 449-461.
Culi et al. 2003, Cell 112:343-54.
Dann et al. 2001, Nature, vol. 412, 86-90.
Erickson et al. Mar. 1973, Journal of Lipid Research, vol. 14:133-137.
Gao, Yuan et al., May 18, 2004, PNAS, vol. 101, No. 20, pp. 7618-7623.
Glinka et al, 1998, Nature 391(6665):357-62.
Glinka et al, Jun. 10, 2002, DKFZ 2001: Research Report 1999/2000: 36-40.
Gong et al. 2001, Cell 107:513-23.
Gumbiner et al. 1998, 8:430-5 Curr Opin Genet Dev.
Guo, Nini et al. Jun. 22, 2004, vol. 101, No. 25, pp. 9277-9281.
Graham et al. 2000 Cell. 103(6):885-96.
Gruneberg, et al. 2001, Angew. Chem. Int. Ed Engl. 40, 389-393.
Hey et al. 1998. Gene 216, 103-11.
Hsieh et al. 2003, Cell 112:355-67.
Hsu et al. 1998, Molecular and Cellular Biology 18:4807-4818.
Hurst 1994 J. Chem. Inf. Comput. Sci. 34, 190-196.
Jeon et al. 2001, Nat Struct Biol 8:499-504.
Kalajzic et al. 2002, J Bone Miner Res 17(1):15-25.
Kannus et al. 2000, Osteoporos Int 11:443-8.
Kato et al. 2002, J Cell Biol 157(2):303-14.
Krupnik et al. 1999, Gene 238:301-13.
Leyns et al. 1997, Cell, vol. 88, 747-756.
Li et al. 2002, J Biol Chem 277(8):5977-81.
Li et al. 1999, EMBO J 18:4233-4240.
Li et al. 1999, J. Biol. Chem. 274:129-134.
Lilien, Ryan H. et al., Mar. 4, 2004 Dartmouth Computer Science Dept. Technical Report No. TR2004-492 at http://www.cs.dartmouth.edu/reports/reports.html.
Lips, 1997, Am J Med 103:3S-8S; discussion 8S-11S.
Little et al. 2002, Am J Hum Genet 70:11-9.
Love et al, 1995, Nature. 376(6543):791-5.
Mao et al. 2002, Nature 417:664-7.
Mao et al, 2001, Mol Cell 7:801-9.
Monaghan 1999, Mech Dev 87:45-56.
Moon RT et al, 1997, Cell, vol. 88, 725-728.
Nusse 2001, Nature 411:255-6.
Pandur et al, 2001, Bioessays 23:207-10.
Pfaffl 2001, Nucleic Acids Res May 1, 2001;29(9):e45.
Pinson et al, 2000, Nature 407:535-538.
Poy 2001, Nat Struct Biol. 8(12):1053-7.
Rarey et al, 1996 J. Mol. Biol. 261: 470-479.
Reddy, Seshamma T., et al. 2004 J Invest Dermatol 123:275-282.
Schweizer et al, 2003, BMC Cell Biol 4:4.
Semenov et al, 2001, Curr Biol 11: 951-61.
Szilagyi, Andras et al., Phys.Biol. 2 (2005) 1-16.
Takagi et al, 2003, Nature 424:969-74.
Tamai et al, 2000, Nature 407:530-5.
Tamai et al, 2004, Molecular Cell, vol. 13, 149-156.
Tolwinski et al, 2003, et al, Dev Cell 4:407-18.
Toogood, Peter L. Apr. 11, 2002, Journal of Medicinal Chemistry vol. 45, No. 8, pp. 1543-1558.
Van Wesenbeeck et al, 2003, Am J Hum Genet 72:763-71.
von Kries et al, 2000, Nat Struct Biol. 7(9):800-7.
Waszkowycz, et al, 2001, IBM Systems J. 40, 360-376.
Wang, et al., 2005 Journal of Medicinal Chemistry, vol. 48, No. 7, 2432-2444.
Wehrli, et al, 2000, Nature 407:527-30.
Wharton 2003, Dev Biol. 253(1):1-17.
Wodarz 1998, Annu. Rev. Cell Dev. Biol. 14:59-88.
Wong et al, 2003, Mol Cell. 12(5):1251-60.
Wong et al, 2000, Nat Struct Biol. 7(12):1178-84.
Xing Y et al, 2003, Genes Dev. 2003, Nov. 15;17(22):2753-64.
Zuckerman 1996, N Engl J Med 334:1519-25.
Reya et al, 2005 Nature 434: 843.
Kleber et al, 2004 Curr Opin Cell Biol 16:681.
Logan et al, 2004 Annu Rev Cell Dev Biol 20: 781.
Sancho et al, 2004 Annu Rev Cell Dev Biol 20: 695-723.
Wang et al, 2004 Curr Opin Genet Dev 14: 533.
Moon et al, 2004, Nat Rev Genet 5:691.
Kawano et al, 2003, J Cell Sci 116: 2627.
Zhang et al., 2004, Mol Cell Biol 24:4677-4684.
Fujino et al., 2003, Proc Natl Acad Sci USA 100: 229.
Yamazaki et al, 2003, Biochem Biophys Res Commun 304: 229.
Hoffmann et al., 1999, J Med Chem 42: 4422.
Kramer 1999, Proteins 37: 228.
Mundy et al., 1999, Science 286: 1946.
Dunstan et al., 1999, J Bone Miner Res 14:953.
Li, et al, 2001, Cell Mol Life Sci 58: 2085.
Smith, 1999, Trends Biochem Sci 24: 181.
Yuan et al, 1999, J. Biol. Chem. 274: 30419-30423.
Li et al, 2002, JBC 277; 5977-5981.
Li et al., 2005, JBC vol. 280, No. 20, 19883-19887.
Wei et al. 2006, Cell 124; 1141-1154.
Johnson et al., 2004, J Bone Disease and Mineral Research 19; 1749-1757.
Hay et al. 2005, JBC 280; 13616-13623.
Kikuchi et al., 2006, Exp Molec. Med 38; 1-10.
Semenov et al. 2005, JBC 280; 26770-26775.
Streeten et al., 2008, Bone 43(2008) 584-590.
Krane 2005, J Exp Med 201; 841-843.
Krishnan et al., 2006, J Clin Invest 116; 1202-1.
Liang et al., 2003, Cancer Cell 4:349-360.
Weeraratna et al., 2002, Cancer Cell 1:279-288.
Polakis 2000 Genes Dev 14: 1837-1851.
Behrens and Lustig 2004 Int J Dev Biol 48: 477-487.
Luu et al., 2004 Curr Cancer Drug Targets 4; 653-671.
Bafico et al., 2004 Cancer Cell 6; 497-506.
Janssens et al., 2006 Investigational New Drugs 24; 263-280.
Tian et al. 2003 NEJM 349: 2483-2494.
Oshima et al., 2005 Blood 106: 3160-3165.
Toomes et al, 2004 Am. J. Hum. Genet. 74: 751-730.
Niemann et al., 2004 Am J. Hum. Genet 74: 558-563.
Grant et al., 2006, Nature Genetics 38: 320-323.
Rodova et al., 2002 J. Biol. Chem 277: 29577-29583.
Chilosi et al., 2003, Am J. Pathol. 162: 1495-1502.
Cheon et al., 2002 Proc. Nat. Acad. Sci. (USA) 99: 6973-6978.
Miyaoka et al., 1999 Schizophr. Res. 38:1-6.
Symolon et al. 2004 J. Nutr. 134: 1157-1161.
Chen H. et al. Cell 84: 491-495, 1996.
Lee G.H. Nature 379: 632-635, 1996.
Nusse and Varmus 1982, Cell 31:99-109.
Couso et al., 1995 Development 120: 621-636.
Mukhopadhyay et al., 2001 Dev Cell 1:423-434.
Li et al., 2005 Nature Genetics 37:945-952.
Mukhopadhyay et al., 2006 Development 133:2149-2154.
Pinson et al., 2000 Nature 407:535-538.
Magoori et al., 2003 J Biol Chem 278:11331-11336.
Van Amerongen and Burns, 2006 Trends Genet 12:678-389.
Bockamp et al., 2002 Physiol Genomics 11:115-132.
Raport et al., 1996 J. Biol Chem 271:17161-17166.
Deng et al., 1996 Nature 382:661-666.
Dragic et al., 1996 Nature 381-667-673.
Abrami et al., 2003 J. Cell Biol 160:321-328.
Bradley et al., 2001, Nature 414:225-229.
Scobie et al., 2003 Proc Nat Acad Sci USA 100:5170-5174.
Molloy et al., 1992 J. Biol Chem 267:16396-16402.
Petosa et al., 1997 Nature 385:833-838.
Chauhan and Bhatnagar 2002, Infect Immunol 70:4477-4484.
Cunningham et al., 2002 Proc Nat Acad Sci USA 99:7049-7083.
Pannifer et al., 2001 Nature 414:229-233.
Elliot et al., 2000 Biochemistry 39:6706-6713.
Lacy et al.,2002 J. Biol Chem. 277:3006-3010.
Rosovitz et al., 2003 J. Biol Chem. 278:30936-30944.
Little et al., 1988 Infect Immun 56:1807-1813.
Lacy et al., 2004 Proc Nat Acad Sci USA 13147-13151.
Liu et al., Apr. 2007 Cell Microbiol 9(4):977-987.
Moayeri et al., 2006 Antimicrob Agents and Chemotherapy 50:2658-2665.
Schepetkin et al., 2006 J. Med. Chem. 49:5232-5244.

(56) References Cited

OTHER PUBLICATIONS

Goldman et al., 2006 BMC Pharmacology 6:8-15.
Panchal et al., 2004 Nat Struct Mol Biol 11:67-72.
Forino et al., 2005 Proc Nat Acad Sci USA 102:9499-9504.
Johnson et al., 2006 J. Med. Chem. 12:27-30.
Turk et al., 2004 Nat Struct Mol Biol 11:60-66.
Kocer et al., 2005 Infection and Immunity 73:7548-7557.
Karginov et al., 2005 Proc Nat Acad Sci USA 102:15075-15080.
Opal et al., 2005 Infect Immun 73:5101-5105.
Komiyama et al., 2005 Antimicrob Agents Chemotherapy 49:3875-3882.
Basha et al., 2006 Proc Nat Acad Sci USA 103:13509-13513.
E.L. Eliel & S.H. Wilen, Stereochemistry of Carbon Compounds, John Wiley & Sons, New York, NY, 1994, pp. 1119-1190.
Simon-Chazottes et al., 2006 Genomics 87:673-677.
Erlanson et al., 2004 J. Med Chem. 47:3463-3482.
Erlanson, 2006 Curr Opin Biotech 17:643-652.
Morrisey, 2003 Am J Path 162:1393-1397.
Pongracz and Stockley 2006 Respiratory Research 7:15.
Tickenbrock 2006 J Leuk Biol 79:1306-1311.
Figueroa et al., 2000 J. Histochem & Cytochem, 48(10):1357-1368.
Sen et al., 2000 Proc Nat Acad Sci USA 2791-2796.
Nakamura et al., 2005 Am J Path 167:97-105.
Gustafson and Smith 2006 J. Biol Chem 281:9507-9516.
Cawthorn et al., 2007 Cell Death Differ 14:1361-1373.
Diarra et al., 2007 Nature Medicine 13:156-163.
Rothbacher and Lemaire 2002 Nature Cell Biology 4:E172-E173.
Liu et al., 2003 Molec and Cell Biol 23:5825-5835.
Andl et al., 2002 Developmental Cell 2:643-653.
Sick et al., 2006 Science 1447-1450.
Tamamura et al., 2005 J. Biol Chem. 280:19185-19195.
Hertz and Strickland, 2001 J. Clin. Invest. 108:779-784.
Zeng et al. 2008 Development 135:367-375.
Nam et al., 2006 JBC 281(19):13247-13257.
Mercurio et al., 2003 Development 131:2137-2147.
Swiatek et al., 2006 J. Biol Chem 281:12233-12241.
Zilberberg et al., 2004 J. Biol Chem 279:17535-17542.
Guo et al., 2006 J Med Genet 43:798-803.
Mani et al., 2007 Science 315:1278-1282.
He et al., 2005 Development 131:1663-1677.
Wu et al., 2000 Curr Biol 10:1611-1614.
Zorn, 2001, Curr Biol 11:R592-R595.
Brott and Sokol, 2002 Molec and Cell Biol 22:6100-6110.
Mikels and Nusse, 2006 PloS 4:0570-0582.
Johnson et al., 2006 Genomics 88:600-609.
Pukrop et al., 2006 Proc Natl Acad Sci USA 103:5454-5459.
Lin et al., 1994 Anal Record 240:492-506.
Miyauchi et al., 2001 Histochem Cell Biol 116:57-62.
Elbashir, S. M. et al. Duplexes of 21-nucleotide RNAs mediate RNA interference in cultured mammalian cells. *Nature* 411, 494-8 (2001).
Brummelkamp, T. R., Bernards, R. & Agami, R. A system for stable expression of short interfering RNAs in mammalian cells. *Science* 296, 550-3 (2002).
Kahler, R. A. & Westendorf, J. Lymphoid enhancer factor-1 and bet-acatenin inhibit Runx2-dependent transcriptional activation of the osteocalcin promoter. *J Biol Chem* vol. 278, No. 14, 11937-44 (2003).
Mundlos, S. et al. Mutations involving the transcription factor CBFA1 cause cleidocranial dysplasia. *Cell* 89, 773-9 (1997).
Otto, F. et al. Cbfal, a candidate gene for cleidocranial dysplasia syndrome, is essential for osteoblast differentiation and bone development. *Cell* 89, 765-71 (1997).
Komori, T. et al. Targeted disruption of Cbfal results in a complete lack of bone formation owing to maturational arrest of osteoblasts. Cell 89, 755-64 (1997).
Ducy, P., Zhang, R., Geoffroy, V., Ridall, A. 1. & Karsenty, G. Osf2/Cbfa1 : a transcriptional activator of osteoblast differentiation. *Cell* 89, 747-54 (1997).

Pandur, P., Lasche, M., Eisenberg, 1. M. & Kuhl, M. Wnt-11 activation of a non-canonical Wnt signaling pathway is required for cardiogenesis. *Nature* 418, 636-41 (2002).
Zhang, J, et al. Identification of the haematopoietic stem cell niche and control of the niche size. Nature 425, 836-841 (2003).
Itoh, K., Antipova, A., Ratcliffe, M. J. & Sokol, S. Interaction of dishevelled and Xenopus axin-related protein is required for Wnt signal transduction. *Mol Cell Biol* vol. 20, No. 6, 2228-38 (2000).
Calvi, L, et al. Osteoblastic cells regulate the haematopoietic stem cell niche. Nature 425, 841-846 (2003).
Li, Song et al., A computer screening approach to immunoglobulin superfamily atructures and interactions: Discovery of small non-peptidic CD4 inhibitors as novel immunotherapeutics, Proc Natl Acad Sci USA vol. 94, pp. 73-78, Jan. 1997.
Willert, K, et al. Wnt proteins are lipid-modified and can act as stem cell growth factors. Nature 423, 448-452 (2003).
Gregory, C, et al. The Wnt signaling inhibitor Dickkopf-1 is required for re-entry into the cell cycle of human adult stem cells from bone marrow. The Journal of Biological Chemistry 278, (30):28067-28078 (2003).
Teitelbaum, S, et al. Genetic Regulation of osteoclast development and function. Nature Genetics 4, 638-649 (2003).
Prockop, D, et al. One strategy for cell and gene therapy: Harnessing the power of adult stem cells to repair tissues. PNAS 100, Supp. 1, 11917-11923 (2003).
Brossay, L. et al. CD1d-mediated recognition of an α-galactosylceramide by natural killer T cells is hightly conserved through mammalian evolution. J. Exp. Med. 188,(8): 1521-1528 (1998).
Van der Vliet, H., et al. Potent expansion of human natural killer T cells using α-galactosylceramide (KPN7000)-loaded monocyte-derived dendritic cells, cultured in the presence of IL-7 and IL-15. J. Immunol. Methods 247, 61-72 (2001).
Taichman R.,et al. The Hematopoietic Microenvironment: Osteoblasts and The Hematopoietic Microenvironment. Hematol. 4(5):421-426 (2000).
Rattner A, et al. A family of secreted proteins contains homology to the cysteine-rich ligand-binding domain of frizzled receptors. PNAS. 94(7):2859-63. (1997).
Yamane T., et al. Wnt Signaling Regulates Hemopoiesis through Stromal Cells. J. Immunology. 167:765-772. (2001).
Johnson et al., Journal of Bone and Mineral Research, Nov. 2004, vol. 19, No. 11:1749-1757.
Gallager, 1990, Metabolism, vol. 39, issue 4, supplement 1, Apr. 1990, pp. 27-29, abstract only.
DTP Datawarehouse Index Results, from http://dtp.nci.nih.gov/dtpstandard/servlet/dwindex?searchtype=NSC& outputformat=html& searchlist=366218 accessed Dec. 3, 2007.
In Vivo Models, http://dtp/nci.nih.gov/docs/invivo/invivomodels. html, accessed Dec. 3, 2007, p. 33 only of 55 provided.
NCI Communication re InVivo screening: email From: Daniel Zaharevitz[zaharevitz@dtpax2.neicrf.gov], Sent: Tuesday, Dec. 4, 2007 5:37 PM, to: Gamett, Daniel C., Subject: Re: In vivo screen data, p. 1 of 1.
NCI In Vivo Screening Data http://dtp.nci.nih.gov/dtpstandard/servlet/InvivoSereen?testshortname=tumor+PS ... Accessed Dec. 3, 2007.
NSC668036-Substance Summary, http://pubchem.ncbi.nlm.nih.gov/summary/summary.cgi?sid=512577&loc=ec_rcs; viewed Oct. 30, 2008.
Reya and Clevers, Nature 2005;434:843-850.
Suzuki et al., Nature Genetics 2004,36:417-422.
Itahana et al., Mol Cell. Nov. 2003;12(5):1251-1260.
Barker and Clevers, Nature Reviews: Drug Discovery 2006;5:997-1014.
Clark, Robert D., Consensus Scoring for Ligand/Protein Interactions, Journal of Molecular Graphics and Modeling, 2002,281-295,20.
Dale, Trevor C., Signal Transduction by the Wnt Family of Ligands, Biochem. J., 1998,209-223,329.
Daniels, Danette L., ICAT inhibits beta-catenin binding to Tcf/Lef-family transcription factors . . . Molecular Cell, 2002,573-584,10.
Logan and Nusse, The Wnt Signaling Pathway in Development and Disease, Annu. Rev. Cell. Dev. Biol., 2004,781-810, 20.

(56) References Cited

OTHER PUBLICATIONS

Kelly, Olivia G., The Wnt Co-Receptors-LRP5 and LRP6 are Essential for Gastrulation in Mice, Development 2004,2803-2815, 131.

Mao, LDL-receptor-related protein 6 is a receptor for Dickkopf proteins, Nature, 2001, 321-325, 411.

Mi and Johnson, Role of the Intracellular Domains of LRP5 and LRP6 in Activating the Wnt Canonical Pathway, Journal of Cellular Biochemistry, 2005,328-338,95.

Mi, K.,The low density lipoprotein receptor-related protein 6 interacts . . . The Journal of Biological Chemistry, 2006,4787-4794, 281(8).

Surendran, A role for Wnt-4 in renal fibrosis, Am J Physiol Renal Physiol, 2002,F431-441, 282.

Zeng, X., A Dual-Kinase Mechanism for Wnt Co-Receptor Phosphorylation and Activation, Nature, 2005,873-877,438(8).

Davidson, G.,Casein kinase1 couples wnt receptor activation to cytoplasmic sugnal transduction, Nature 2005,867-872,438(8).

Papakonstantinou, E., Matrix metalloproteinases of epithelial origin in facial sebum in patients with acne . . . , J. Invest Dermatol 2005,673-684,125.

Wang, J. Hierarchical database screening for HIV-1 reverse transcriptase using a pharmacophore model . . . ,J Med Chem. 2005, 2432-2444, 48(7).

Kitagaki et al., Activation of beta—catenin-LEF/TCF signal pathway in chondrocytes stimulates ectopic endochondral ossification, Osteoarthritis and Cartilage 2003, 36-43, 11.

Otto et al., Tomorrow's skeleton staff: mesenchymal stem cells and the repair of bone and cartilage, Cell Prolif. 2004, 97-110, 37.

U.S. Appl. No. 09/356,294, filed Jul. 16, 1999, Rabbani et al.

U.S. Appl. No. 08/574,443, filed Dec. 15, 1995, Rabbani et al.

U.S. Appl. No. 60/965,279, filed Aug. 2007, Wu et al.

\* cited by examiner 2D structure of compounds NCI106164 (A), NCI39914 (B) and NCI660224 (C).

A

B

C 2D structure of anthra-9,10-quninone (A) , NCI 657566 (B)
and the template for the second 2D similarity search (C)

A

B 2D structure of compounds NCI366218 (A, IIC8) and NCI8642 (B, IIIC3) which can specifically interrupt DKK1-LRP5_3 interaction and reverse the inhibition of Wnt signaling by DKK1.

US 8,637,506 B2

COMPOSITIONS AND METHODS FOR BONE FORMATION AND REMODELING

REFERENCE TO RELATED PATENT APPLICATIONS

This application claims the benefit of U.S. Provisional Patent Application No. 60/504,860, filed on Sep. 22, 2003, entitled "Compositions and Methods for Stimulation of Bone Formation."

This application is related to the patent application entitled "Compositions and Methods for the Stimulation or Enhancement of Bone Formation and the Self-Renewal of Cells", by Dan Wu, et al. filed on May 19, 2004, and its entire contents is hereby incorporated by reference, in its entirety.

FIELD OF THE INVENTION

The present invention relates to the field of therapeutic methods, compositions and uses thereof, in the treatment of bone fractures, bone disease, bone injury, bone abnormality, tumors, growths or viral infections. More particularly, the methods and compositions of the invention are directed to the stimulation, enhancement and inhibition of bone formation or bone remodeling.

All patents, patent applications, patent publications, scientific articles, and the like, cited or identified in this application are hereby incorporated by reference in their entirety in order to describe more fully the state of the art to which the present invention pertains.

BACKGROUND OF THE INVENTION

Osteoporosis is a major public health problem, and it is especially prevalent in aging populations (1, 24, 31). The majority of fractures that occur in people over the age of 65 are due to osteoporosis (24, 60). Peak bone mass is a determining factor in establishing the risk of osteoporotic fracture (Heaney et al., 2000), and studies indicate that genetic factors contribute significantly to the variance in peak bone mass. One of the genes that regulate bone mass has recently been identified via positional cloning. Loss of function mutations in low density lipoprotein receptor-related protein 5 (LRP5), a co-receptor for the canonical Wnt signaling pathway (39), were found to be associated with Osteoporosis-Pseudoglioma Syndrome (OPPG), an autosomal recessive disorder which shows a reduction of bone density in humans (14). In addition, two independent kindreds that manifest familial High Bone Mass (HBM) phenotypes were found to harbor a Gly171 to Val substitution mutation (G171V) in LRP5 (5, 32). More recently, additional HBM mutations were reported in the same structural domain of the G171V mutation (51). Moreover, mice in which the LRP5 genes were inactivated by gene targeting showed phenotypes similar to those of OPPG patients (25), and transgenic expression of LRP5G171V in mice resulted in HBM (2). Furthermore, mouse primary osteoblasts showed reduced responsiveness to Wnt in the absence of LRP5 (25), and Wnt (14) or activated β-catenin (4) stimulated the canonical Wnt signaling activity and induced the production of the osteoblast marker alkaline phosphatase (AP) in osteoblast-like cells. Together, these pieces of evidence indicate that the canonical Wnt signaling pathway plays an important role in the regulation of bone development.

Until recently, the canonical Wnt signaling pathway was believed to start when Wnt bound to frizzled Fz proteins. The seven transmembrane domain-containing Fz proteins suppress the Glycogen synthase kinase 3 (GSK3)-dependent phosphorylation of β-catenin through ill-defined mechanisms involving Dishevelled proteins. This suppression leads to the stabilization of β-catenin. β-catenin can then interact with transcription regulators, including lymphoid enhancing factor-1 (LEF-1) and T cell factors (TCF), to activate gene transcription (10, 15, 56). Recently, genetic and biochemical studies have provided solid evidence to indicate that co-receptors are required for canonical Wnt signaling in addition to Fz proteins (39, 40). The fly ortholog of LRP5/6 (LRP5 or LRP6), Arrow, was found to be required for the signaling of Wg, the fly ortholog of Wnt-1 (54). LRP5 and LRP6 are close homologues which basically function the same way, yet exhibit, different expression patterns. In addition, LRP6 was found to bind to Wnt 1 and regulate Wnt-induced developmental processes in *Xenopus* embryos (48). Moreover, mice lacking LRP6 exhibited developmental defects that are similar to those caused by deficiencies in various Wnt proteins (42). Furthermore, LRP5, LRP6 and Arrow were found to be involved in transducing the canonical Wnt signals by binding Axin and leading to Axin degradation and β-catenin stabilization (30, 50). The LRP5/6-mediated signaling process does not appear to depend on Dishevelled proteins (28, 45). Recently, a chaperon protein, Mesd, was identified as required for LRP5/6 transport to the cell surface (9, 19).

*Xenopus* Dickkopf (Dkk)-1 was initially discovered as a Wnt antagonist that plays an important role in head formation (13). Thus far, four members of Dkk have been identified in mammals (26, 37). These include Dkk1, Dkk2, Dkk3 and Dkk4. Dkk1 and Dkk2 inhibit canonical Wnt signaling by simultaneously binding to LRP5 or LRP6 and a single transmembrane protein Kremen (3, 34, 35, 46). It has been previously reported that the LRP5 HBM G171V mutation appeared to attenuate Dick 1-mediated antagonism to the canonical Wnt signaling (5). The present invention describes the mechanism for this attenuation.

SUMMARY OF THE INVENTION

The present invention describes a model which explains the functional interactions of cavities on domains of receptors or co-receptors involved in bone formation or bone remodeling with Dkk, Wnt, Mesd, or other proteins which function in similar ways. These receptors include, but are not limited to, the LRP5 receptor, the LRP6 receptor, and the frizzled receptor. The LRP5 receptor is comprised of four YWTD repeat domains. Each domain contains multiple YWTD repeats of amino acids. The LRP5 receptor also has an LDL receptor repeat. Both LRP5 and LRP6 are close homologues and function in basically the same way although they possess different expression patterns.

The invention provides methods for identifying non-native or exogenous compounds which bind to or interact with these cavities to cause the stimulation, inhibition or regulation of Wnt signaling, and thus bone formation, tumorigenesis and any other biological and pathological process regulated by Wnt signaling. A non-native compound comprises a compound that is not naturally or normally found in a cell or organism, as opposed to a native compound which is not introduced from an outside source. The compounds were identified from a National Cancer Institute (NCI) database through various screening methods and assays. These compounds could also be modified to create derivates or analogues not found in the NCI database or in nature which also function effectively. Compounds were identified which disrupted Dkk and LRP5/6 interactions, Wnt and LRP5/6 interactions and Mesd and LRP5/6 interactions.

BRIEF DESCRIPTION OF THE DRAWINGS

FIG. 2E confirms that the G171V mutation interferes with cell surface transport of LRP5 through the use of a binding assay which detects LRP5 on the cell surface. The levels of cell surface LRP5 molecules were detected by Western analysis using streptavidin-horse radish peroxidase (SA-HRP) after the cell surfaces were biotinylated and LRP5 molecules were precipitated with anti-HA antibody (FIG. 2E, upper panel). The levels of LRP5 in the immunocomplexes are shown in the lower panel of FIG. 2E.

FIG. 3B shows that when HEK cells were transfected with LEF-1 luciferase reporter plasmids, Wnt-1, Dkk1 and Kremen in the presence of Wt or G171V LRP5 as indicated in the figure. LEF-1 reporters-indicated Wnt activity is significantly higher in HEK cells expressing $LRP5_{G171V}$ than those expressing $LRP5_{Wt}$ when Dkk is present. The protein expression levels of Dkk1, Kremen and LRP5 were verified by Western blotting, as shown in FIG. 3C.

FIG. 4B shows equal amounts of Wt and mutant LRP5 expression after transfection.

Figure 5:
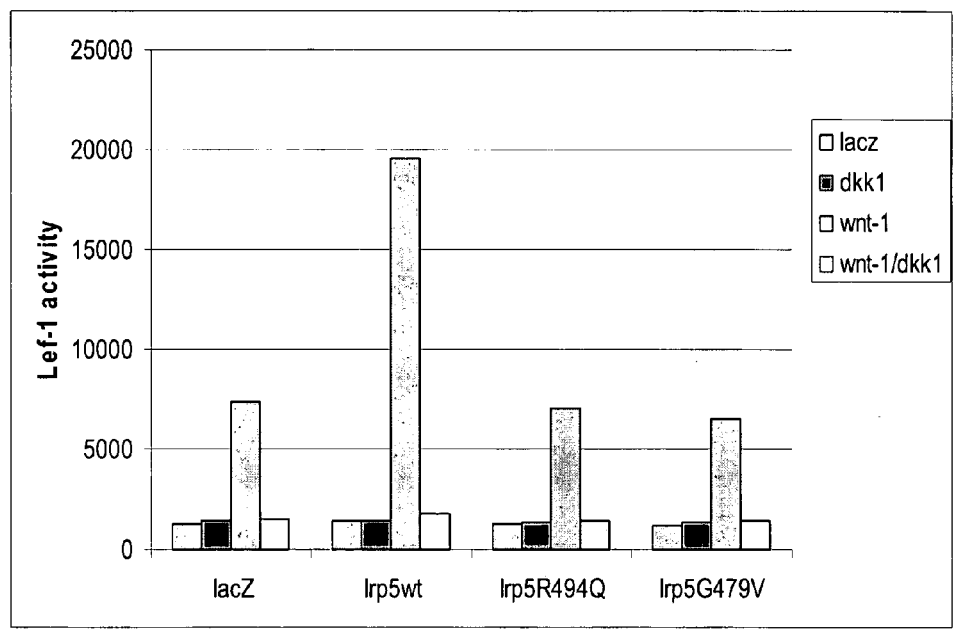
FIG. 5 shows that the second domain of LRP5 is required for Wnt activity. HEK cells were transfected with LEF activity reporter plasmids and expression plasmids. One day later, LEF reporter activity was measured, as previously described.

The results in FIG. 5 show that $LRP5_{R494Q}$ and $LRP5_{G479V}$ (LRP5 with point mutations in the second domain) may abolish Wnt signaling compared to $LRP5_{Wt}$.

Figure 6:
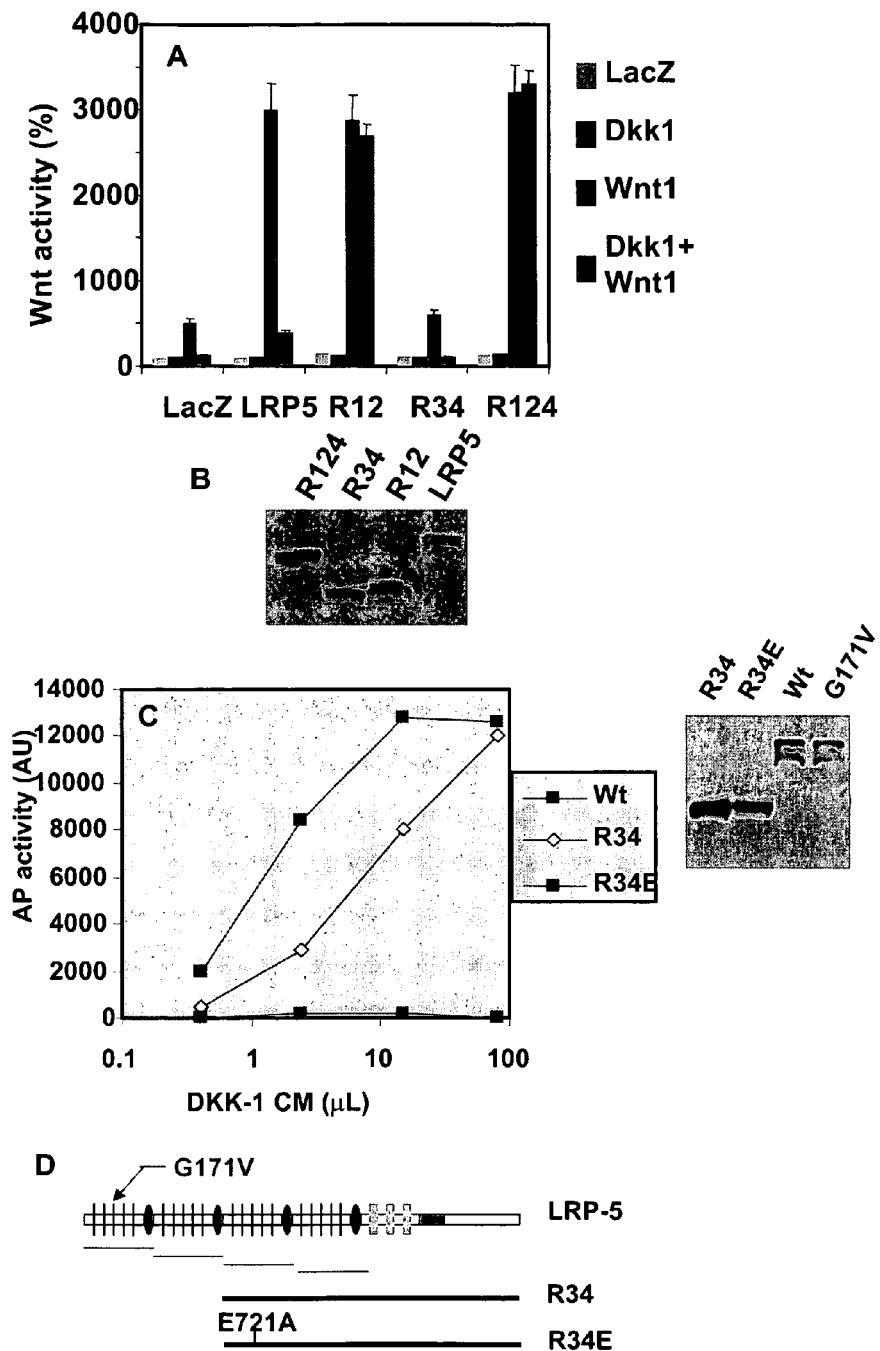

FIG. 6 illustrates that the third domain of LRP5 is required for Dkk-mediated antagonism. FIG. 6A shows that the third YWTD repeat domain is required for Dkk-mediated inhibition. HEK cells were transfected with LEF activity reporter plasmids, Kremen1 plasmids and expression plasmids. LRP5R12 or LRP5R124, but not LRP5R34, could still potentiate Wnt-stimulated LEF-1 activity, suggesting that either LRP5R12 or LRP5R124 retains the Wnt coreceptor function. However, Dkk1 could not inhibit Wnt signaling when LRP5R12 or LRP5R124 was present despite the coexpression of Kremen. This suggests that the third YWTD repeat domain is required for Dkk1-mediated inhibition. The expression level of $LRP5_{Wt}$ and its mutant molecules are shown in FIG. 6B. FIG. 6C illustrates that LRP5R34 contains Dkk1 binding sites and that E721 in R34 is required for Dkk1 binding. FIG. 6D is a schematic representation of the mutations.

Figure 7:
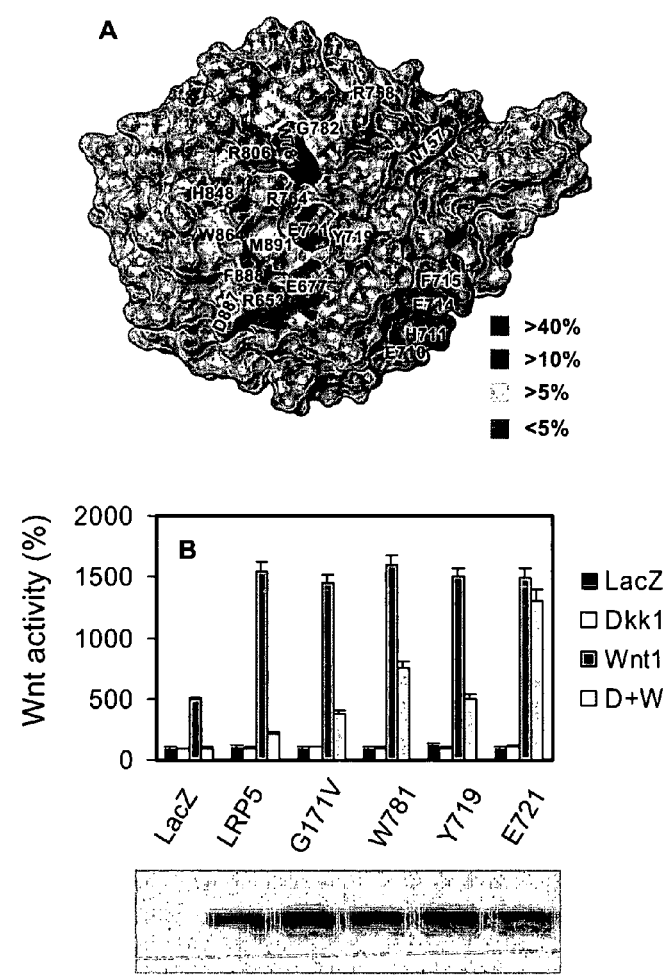

FIG. 7 shows that amino acid residues in the third YWTD repeat domain, consisting of interaction surfaces, are required for Dkk-mediated inhibition of Wnt. In FIG. 7A, the space filled model of the third YWTD repeat domain was deduced based on the structure of the LDL receptor YWTD repeat domain (13). Based on the three-dimensional structure, 19 LRP5 mutants containing Ala substitution mutations on the surface of the third YWTD repeat domain were generated. The ability of these mutant LRP5 proteins to resist Dkk1-mediated inhibition was determined. Nine of the mutants (more than 5%) showed altered sensitivity to Dkk1-mediated inhibition, and they all contained mutations that were localized on the same surface. In FIG. 7B, HEK cells were transfected with LEF activity reporter plasmids, Kremin1 plasmid, and expression plasmids. The expression of Wt and mutant LRP5 molecules are shown in the lower panel. Among 19 mutations, the E721 mutation showed the strongest effect on Dkk1-mediated inhibition of Wnt, followed by W781, and then Y719. $LRP5_{G171V}$ also showed an effect on the Dkk1-mediated inhibition of Wnt.

Figure 8:
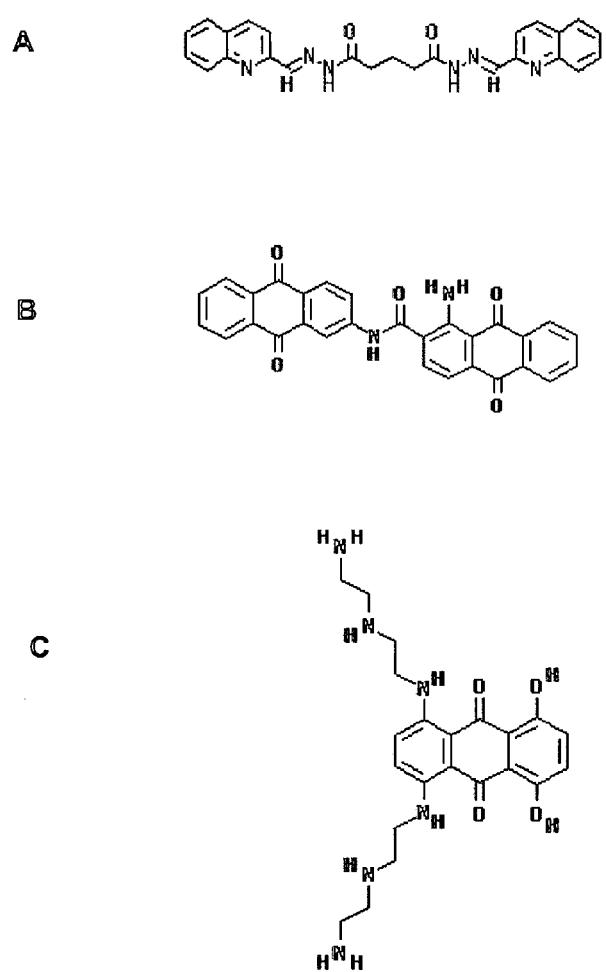

FIG. 8 shows the two dimensional structures of three compounds obtained from the National Cancer Institute (NCI). NCI106164 (FIG. 8A) shows a 68% inhibitory effect on Dkk1 binding while NCI39914 (FIG. 8B) and NCI660224 (FIG. 8C) increase Dkk1 binding by 654% and 276%, respectively.

Figure 9:
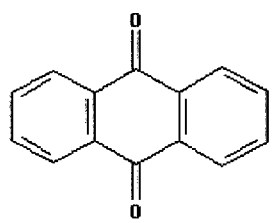
Figure 9:
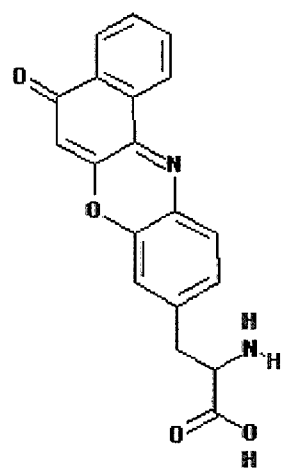
Figure 9:
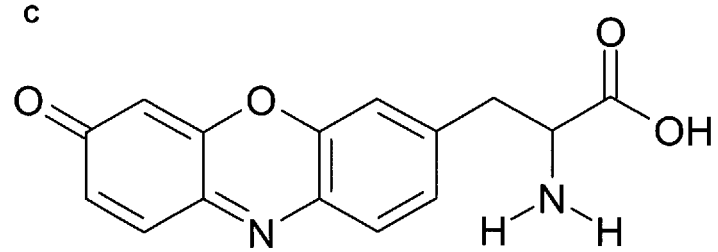

FIG. 9 illustrates the two-dimensional structure of anthra-9,10-quinone (FIG. 9A), a common substructure in NCI39914 and NCI660224. FIG. 9B shows the two-dimensional structure of NCI 657566. FIG. 9C shows the template that was used for the two-dimensional similarity search.

Figure 10:
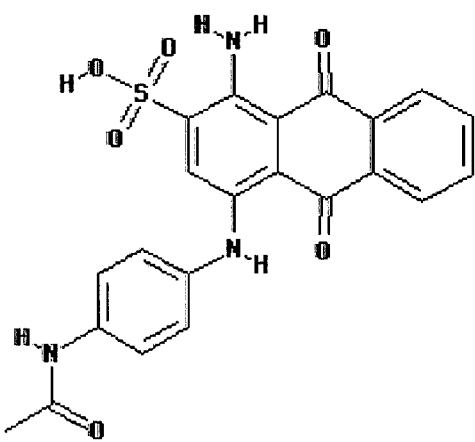
Figure 10:
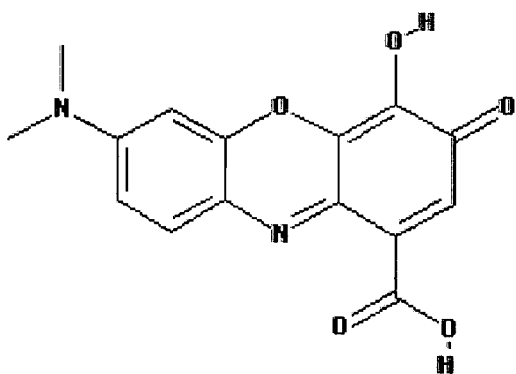

FIG. 10. shows the two-dimensional structure of compounds NCI366218 (IIC8, FIG. 10A) and NCI8642 (IIIC3, FIG. 10B) which specifically interrupt Dkk1-LRP5 interaction and reverse the inhibition of Wnt signaling by Dkk1.

Figure 11:
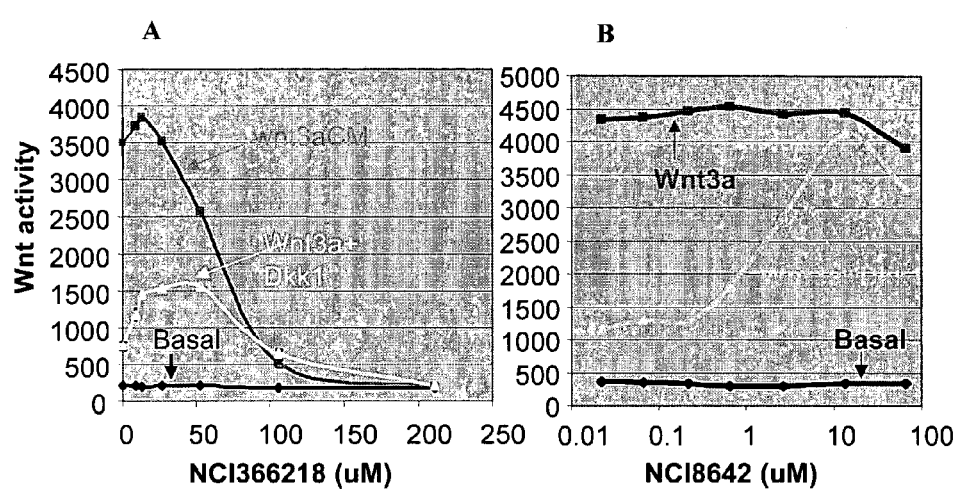

FIG. 11 illustrates that NCI366218 and NCI8642 reverse Dkk1 inhibition. HEK cells were transfected with LRP5 plasmid together with a LEF-1 expression plasmid, LEF-1 luciferase reporter plasmid and a GFP expression plasmid. The cells were then treated with different concentrations of the NCI366218 and NCI8642 compounds and subsequently treated with control CM, Wnt3a CM or Wnt 3a/Dkk1 CM mixture for 6 hrs. The reporter activity from cells treated with DMSO was taken as 100%. FIG. 11 shows that at certain concentrations, NCI366218 (FIG. 11A) and NCI8642 (FIG. 11B) can significantly reverse Dkk-mediated inhibition of Wnt activity.

Figure 12:
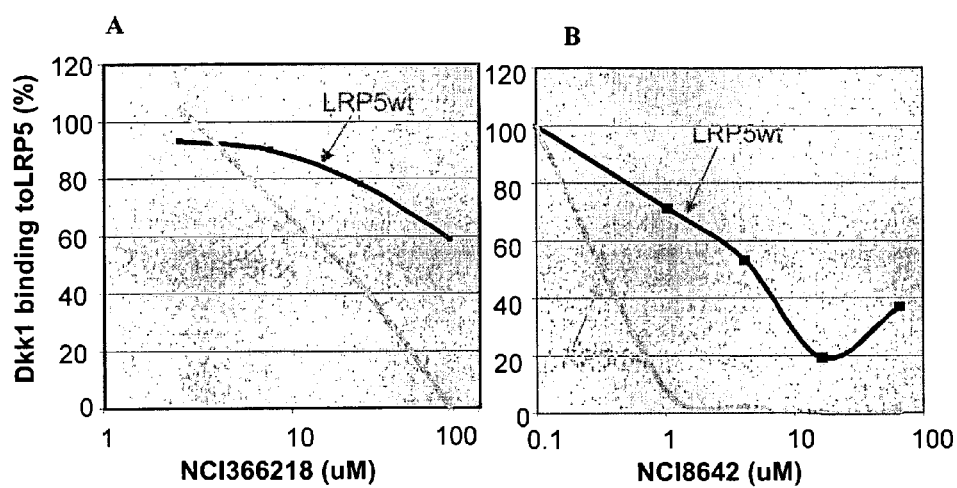

FIG. 12 shows that NCI366218 and NCI8642 can inhibit Dkk1 binding to LRP5. HEK cells were transfected with Mesd plasmids and LRP5 or LRP5R34. One day later, cells were treated with different concentrations of NCI366218 and NCI8642 and incubated on ice with conditioned medium (CM) prepared from HEK cells expressing mDkk1-AP. The AP activity was determined as previously described. The AP activity from cells treated with DMSO was taken as 100%. FIG. 12 shows that NCI366218 (FIG. 12A) and NCI8642 (FIG. 12B) inhibit Dkk1 binding to LRP5 wt, and Dkk protein binding to LRP5R34.

Figure 13:
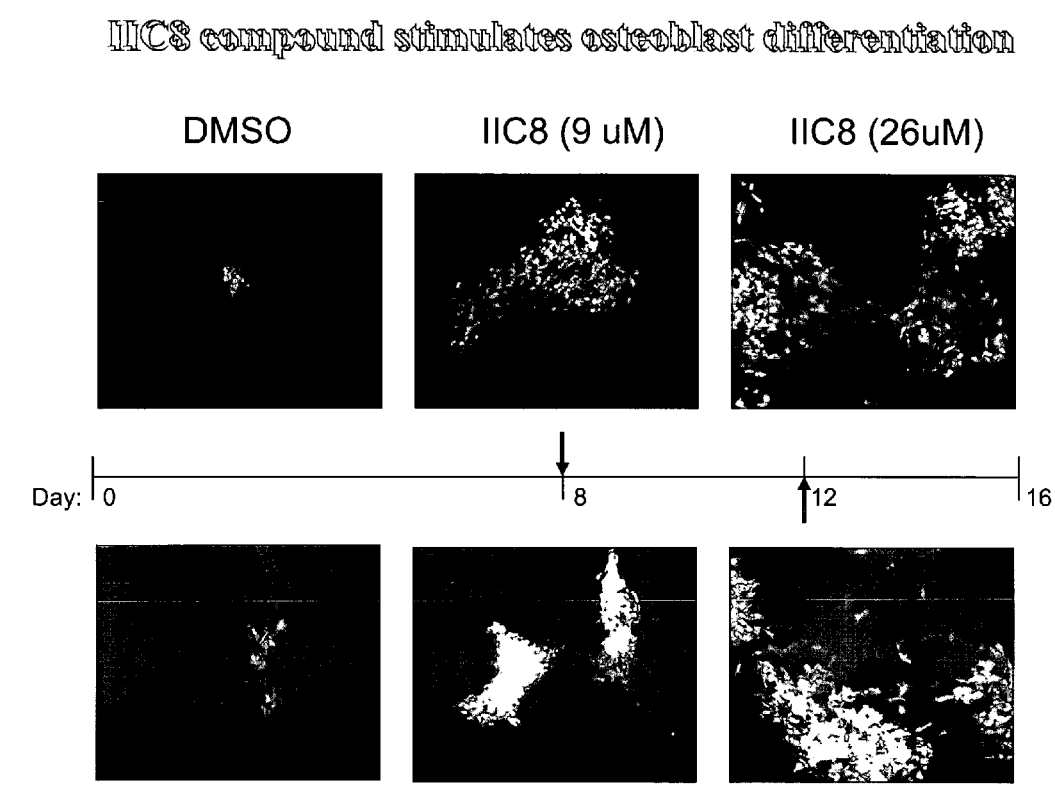

FIG. 13 illustrates that NCI366218 (IIC8) can stimulate osteoblast differentiation. Bone marrow stromal (BMS) cells were isolated from 3-month-old mice carrying a Green Fluorescent Protein (GFP) transgene controlled by the 2.3 Kb ColIA1 promoter (2.3Col-GFP)$^{23}$, in which GFP can be used as a marker of osteoblast cells. On the $8^{th}$ and $12^{th}$ day, cultures were treated with 9 μM and 26 μM of IIC8 compound, respectively. The same time point, cultures were treated with DMSO as the control. FIG. 13 shows that the osteoblast differentiation marker, 2.3Col-GFP, was turned on when BMS culture was treated with IIC8.

Figure 14:
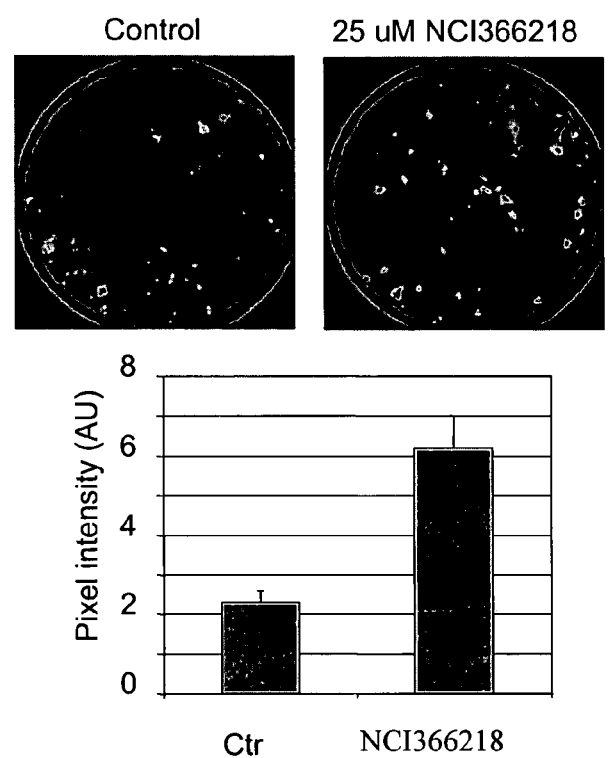

FIG. 14 shows an osteogenic assay. Primary bone marrow stromal osteoblasts were cultured in the presence and absence of NCI366218 and induced into differentiation. 20 days later, mineralization of the osteoblasts reflecting the bone formation process was observed with Xylene Orange staining. NCI366218 stimulated mineralization two fold.

Figure 15:
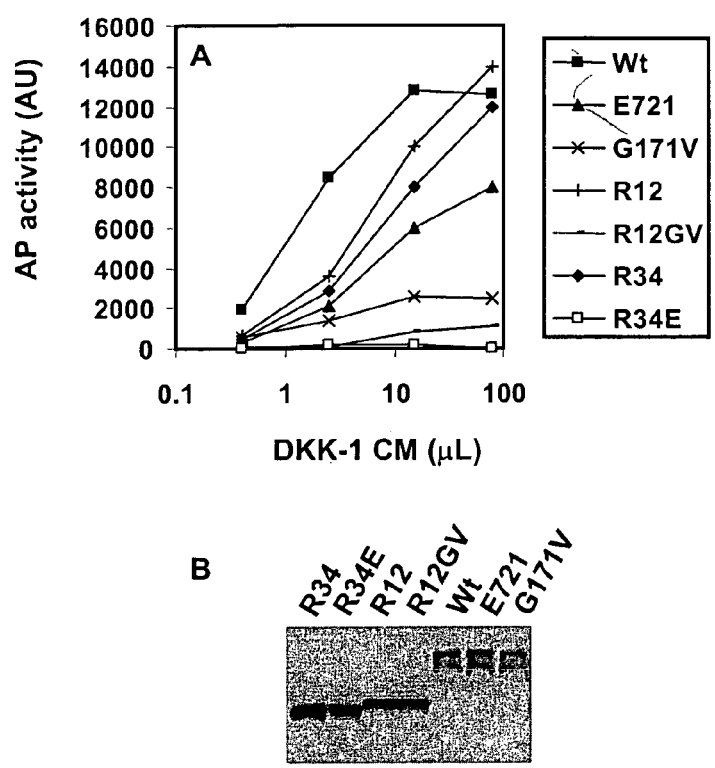

FIG. 15 illustrates that both LRP5R12 and LRP5R34 contain Dkk1 binding sites, E721 in R34 is required for the Dkk1 binding and the G171V LRP5 mutant can abolish the Dkk binding to the cell surface. FIG. 15A shows that Dkk1 can bind to both LRP5R12 and LRP5R34, but the Dkk1 binding to the cell surface was significantly low in cells transfected with R12GV (G171V mutation in LRP5R12) and R34E (LRP5R34 carrying the E721 mutation). FIG. 15B shows equal amounts of Wt and mutant LRP5 expression after transfection.

Figure 16:
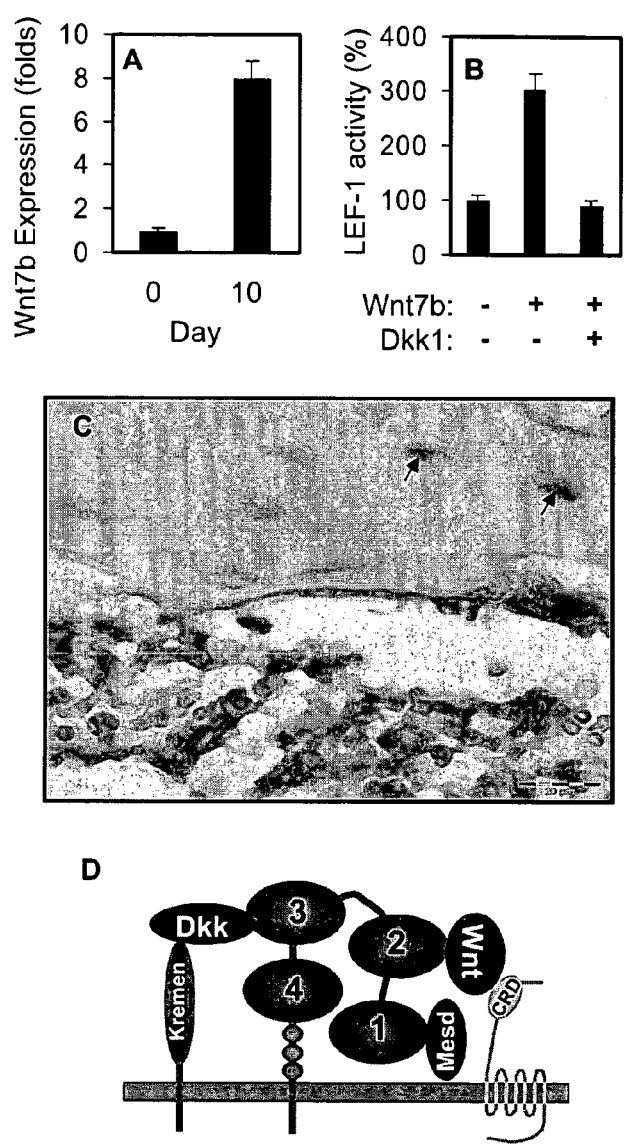

FIG. 16 illustrates Dkk1 and Wnt7b expression in osteogenic cells. Total RNA was isolated from bone marrow stromal cell culture at different time points after differentiation induction. Dkk and Wnt expression level was determined by real time RT-PCR. Wnt7b showed marked increase in its expression after differentiation induction (FIG. 16A). The ability of Wnt 7b to stimulate the LEF-1 reporter gene was examined and it was able to stimulate the canonical Wnt pathway (FIG. 16B). FIG. 16C is mouse long bone section in situ hybridization picture. It shows most of Dkk1 is expressed in osteocyte. FIG. 16D illustrates the interactions between Kremen, Dkk, LRP, Wnt and Fz.

DETAILED DESCRIPTION OF THE INVENTION

Figure 3:
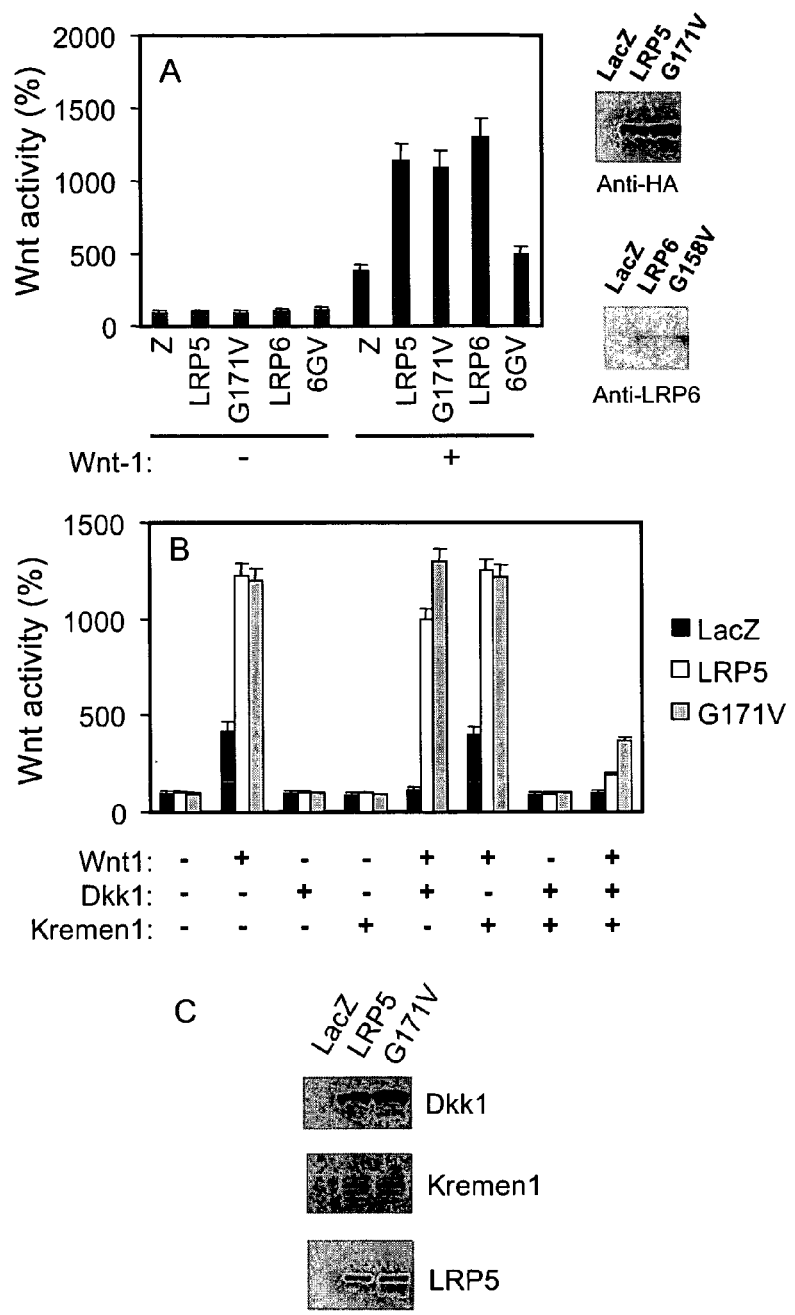
FIG. 3 shows that the HBM G171V mutation of LRP5 is less susceptible to Dkk1-mediated inhibition of coexpressed Wnt activity. The left panel of FIG. 3A shows that when HEK cells were transfected with plasmids as indicated together with LEF-1 luciferase reporter plasmids in the presence or absence of Wnt1, the HBM G171V mutation did not lead to an increase in LEF-1-dependent transcriptional activity compared to the wildtype (Wt) LRP5 ($LRP5_{Wt}$). The right panel of FIG. 3A shows expression levels of LRP5, $LRP5_{G171V}$, LRP6, and $LRP6_{G158V}$ as determined by antibodies specific to the HA tag carried by LRP5 proteins or anti-LRP6 antibodies.

As previously reported (5), expression of the LRP5 mutant protein (LRP5$_{G171V}$) containing the HBM G171V mutation and an HA-epitope tag at its C-terminus (FIG. 3A) did not lead to an increase in LEF-1-dependent transcriptional activity compared to the wildtype (Wt) LRP5 (LRP5$_{Wt}$) (FIG. 3A). Additionally, the G171V mutation did not result in further potentiation of the activity stimulated by coexpressed Wnt1 in an autocrine paradigm (FIG. 3B). LEF-1 is a down-stream target transcription factor of the canonical Wnt signaling pathway. Its activity, measured by a luciferase reporter gene assay, has been widely used to gauge the canonical Wnt activity (20, 30). Thus, LRP5$_{G171V}$ is neither constitutively active nor more competent in transducing Wnt signaling.

Surprisingly, the corresponding mutation on LRP6, a substitution of a Val residue for Residue G-158, rendered it unable to act synergistically with Wnt-1 (FIG. 3A), likely inactivating the receptor.

It was shown that LRP5$_{G171V}$ was less susceptible to Dkk1-mediated inhibition than LRP5$_{Wt}$ in the absence of Kremen (5). Kremen is a Dkk-binding single-transmembrane protein known to facilitate Dkk1-induced inhibition (34). In this study, we tested the effect of this mutation in the presence of Kremen. The coexpression of Kremen1 significantly potentiated Dkk-mediated inhibition (FIG. 3B), confirming the previously reported effect of Kremen (34). Similar to what was observed in the absence of Kremen, in the presence of both Kremen1 and Dkk1, Wnt showed higher activity in HEK cells expressing LRP5$_{G171V}$ than those expressing LRP5$_{Wt}$ (FIG. 3B). To ensure that the difference was not a result of multi-plasmid transfection, the protein expression of Dkk1, Kremin1 and LRP5 (FIG. 3C) was examined. Similar results of increased resistance to Dkk-mediated inhibition of autocrine Wnt1 activity were also observed in NIH3T3 cells and two osteoblast-like cell lines, MC3T3 and 2T3.

Figure 1:
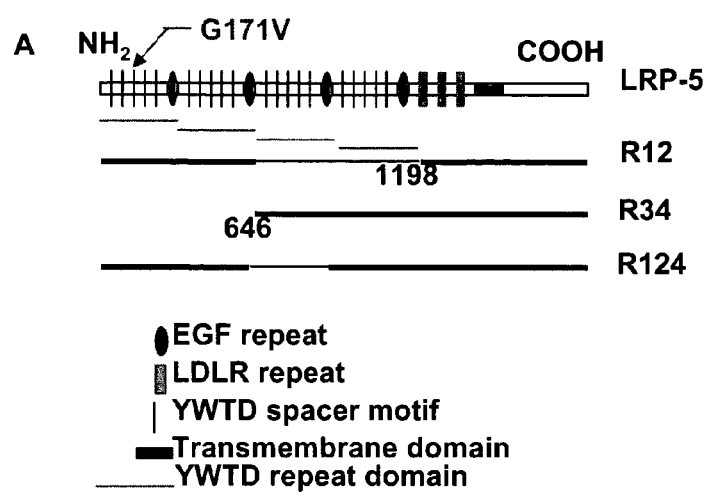
FIG. 1 shows a schematic representation of wildtype LRP5 and its deletion mutants.

The prevailing hypothesis for explaining why LRP5 G171V is less susceptible to Dkk1-mediated inhibition has been that the mutation could disrupt the interaction between LRP5 and Dkk1. It is reasonable to hypothesize that the first YWTD repeat domain that contains G171 is required for Dkk1-mediated antagonism. To test this hypothesis, two LRP5 deletion mutants were generated: LRP5R12 with a deletion of the third and fourth YWTD repeat domains, and LRP5R34 with a deletion of the first and second YWTD repeat domains (FIG. 1). As previously reported for LRP6 (35), LRP5R12, but not LRP5R34, could still potentiate Wnt-stimulated LEF-1 activity (FIG. 6A), suggesting that LRP5R12 retains the Wnt coreceptor function. However, Dkk1 could not inhibit Wnt signaling when LRP5R12 was present even if Kremen was coexpressed (FIG. 6A). This suggests that the last two YWTD repeat domains may be required for Dkk1-mediated inhibition. To further delineate the sequence that is required for Dkk1-mediated inhibition, an additional LRP5 mutant, LRP5R124, was generated in which the third YWTD repeat domain was deleted (FIG. 1). Like LRP5R12, LRP5R124 is also resistant to Dkk1-mediated inhibition (FIG. 6A), indicating that the third YWTD repeat domain is required for Dkk1-mediated inhibition.

As deletion of the entire third YWTD repeat domain may cause gross conformational changes in LRP5, point mutations in this domain were created that could disrupt Dkk1-mediated inhibition. Based on the three-dimensional structure of the third YWTD repeat domain deduced from that of the LDL receptor (22), 19 LRP5 mutants were created containing Ala substitution mutations on the surface of the third YWTD repeat domain (FIG. 7A). The ability of these mutant LRP5 proteins to resist Dkk1-mediated inhibition was determined and is shown in FIG. 3A. Nine of the mutants showed altered (more than 5%) sensitivity to Dkk1-mediated inhibition, and they all contained mutations that were localized on the same surface (FIG. 7A). Among these mutations, the E721 mutation showed the strongest effect, followed by W781, and then Y719 (FIG. 7B). Mutations of E721-corresponding residues in the first and second YWTD repeat domains (D111 and D418, respectively) did not significantly alter the sensitivity to Dkk-mediated inhibition. All the mutants that were resistant to Dkk1-mediated inhibition were also resistant to Dkk2-mediated inhibition. All this data supports the conclusion that the third YWTD repeat domain is required for Dkk-mediated inhibition.

An obvious explanation for the requirement of the third YWTD repeat domain for Dkk-mediated inhibition is that this domain is responsible for Dkk1 binding. The direct binding of Dkk1-AP fusion protein to LRP5 expressed on the surface of HEK cells was measured (34). As shown in FIG. 6C, Dkk1-AP showed a saturating binding curve to HEK cells expressing LRP5. This binding would only be measured when Mesd, a LRP5/6 chaperon that was shown to facilitate the folding and trafficking of LRP5/6 (6, 11, 19), was coexpressed. Surprisingly, $LRP5_{E721}$ still showed significant binding of Dkk1, and the binding was higher than that shown by $LRP5_{G171V}$ (FIG. 6C). $LRP5_{E721}$, which is highly resistant to Dkk1-mediated inhibition compared to $LRP5_{G171V}$ (FIG. 7B), showed better binding of Dkk1 than $LRP5_{G171V}$ (FIG. 6C). To show that the third YWTD repeat domain may indeed bind Dkk1, binding of Dkk1-AP to HEK cells expressing R34 or R34E (R34E is R34 carrying the E721 mutation) was examined. While R34 showed significant binding of Dkk1-AP, R34E failed to do so (FIG. 15A), demonstrating that R34 is capable of binding Dkk1 and that E721 is required for the binding to occur. This may be explained by the observation that the third YWTD repeat domain is not the only site for Dkk binding on LRP5, allowing $LRP5_{E721}$ to retain its ability to bind Dkk1. This explanation was confirmed by observing that R12 could also bind Dkk1 (FIG. 15A). Although both R12 and R34 may bind Dkk1, their affinities for Dkk1 appear to be at least five times less than the affinity of full-length LRP5 (estimated from half maximal binding). Although the maximal binding to cells expressing R12 or R34 appeared to be comparable or probably even higher than that of $LRP5_{Wt}$ (the binding to R12 or R34 did not appear to reach saturation at the maximal possible inputs), the expression levels of R12 and R34, as estimated by Western analysis (FIG. 15B) were approximately twice as much as that of $LRP5_{Wt}$. This, supports the conclusion that there are more than one binding sites for Dkk1 on LRP5 or LRP6.

Figure 2:
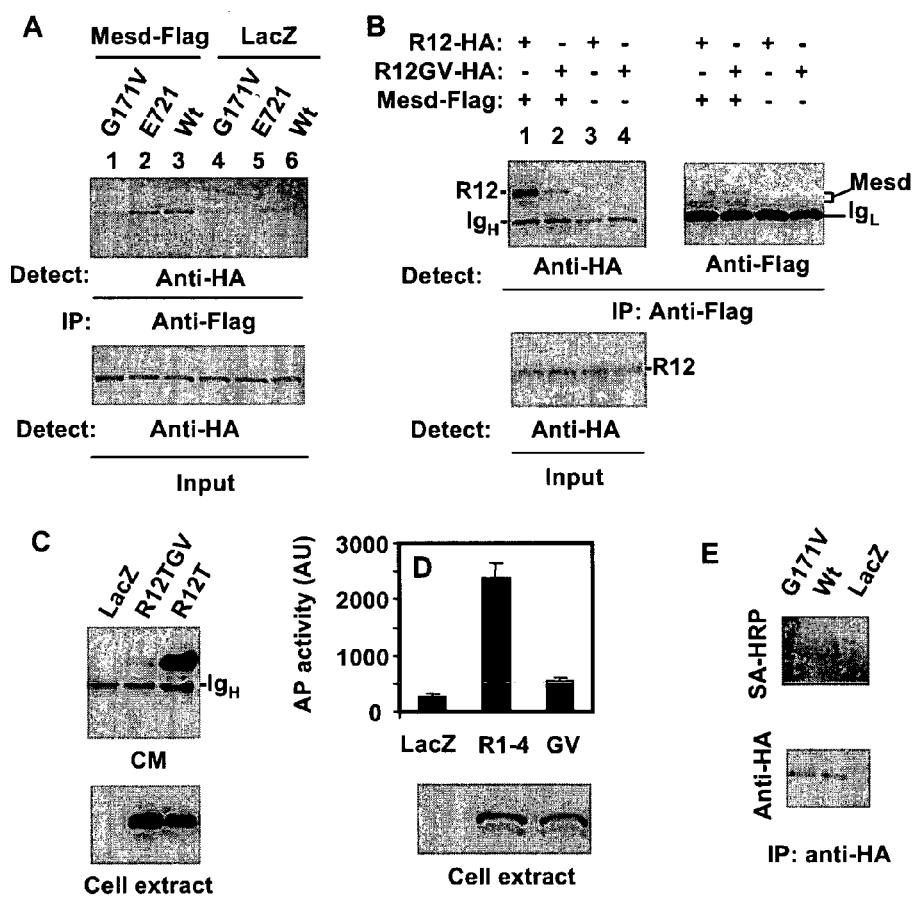
FIG. 2 illustrates that the G171V mutation disrupts LRP5 trafficking. HEK cells were transfected with expression plasmids as indicated in the figure. One day later, the cells were lysed and immunoprecipitation was carried out using an anti-Flag antibody. Mesd was Flag-tagged whereas all LRP5 molecules were HA-tagged. The G171V mutation disrupted the interactions of both LRP5 with Mesd (FIG. 2A, lanes 1 and 3), and R12 with Mesd (FIG. 2B, lanes 1 and 2), while the E721 mutation did not affect the interaction (FIG. 2A, Lanes 2 and 3). The lower panels of FIG. 2A and FIG. 2B show equal amounts of Wt and mutant LRP5 input for the immunoprecipitation. [HEK cells were transfected with the Mesd plasmid and the expression plasmids indicated in the figure.] R12TGV, R12T, R1-4 and R1-4GV (GV) are AP fusion proteins, which are LRP5 mutants lacking transmembrane domains that may be secreted in the supernatants of the cell cultures. One day later, conditioned medium (CM) was collected and centrifuged at a high speed. The supernatants were immunoprecipitated by an anti-HA antibody (FIG. 2C) or used for an AP assay (FIG. 2D). Cells were also lysed in the SDS-PAGE sample buffer and analyzed by Western blotting (lower panels of FIG. 2C and FIG. 2D). The data shows that the G171V mutation inhibited the secretion of R12 and R1-4.

G171V, a point mutation in the first YWTD repeat domain, reduces the apparent binding of Dkk1 drastically (FIG. 6C). The characteristics of the Dkk1 binding curve for $LRP5_{G171V}$ suggest that the G171V mutation does not appear to alter the affinity for Dkk1, despite reducing maximal binding six-fold (FIG. 6C). Although both $LRP5_{Wt}$ and $LRP5_{G171}$ were expressed at similar levels (FIG. 6C), the G171V mutation resulted in fewer LRP5 receptors on the cell surface. Since it is well known that Mesd plays an important role in the transport of LRP5 receptors to the cell surfaces, the G171V mutation was examined to determine whether it interfered with Mesd function. Mesd has previously been shown to interact with LRP5 or LRP6 (19). Consistent with this finding, the co-immunoprecipitation of LRP5 and Mesd was (FIG. 2A). The interaction of R12 with Mesd was also detected (FIG. 2B). The results showed that the G171V mutation disrupted the interactions of both LRP5 with Mesd (FIG. 2A, Lanes 1 and 3) and R12 with Mesd (FIG. 2B, Lanes 1 and 2), while the E721 mutation did not affect the interaction (FIG. 2A, Lanes 2 and 3). If the interaction between LRP5 and Mesd is important for the function of Mesd (folding and transport of LRP5 or LRP6), the G171V mutation should also impede the secretion of LRP5 mutants that lack the transmembrane domains. As expected, the G171V mutation inhibited the secretion of R12T (FIG. 2C) and R1-4 (FIG. 2D), which are R12 and full length LRP5, respectively, lacking the transmembrane and intracellular domains. R1-4, carrying the E721 mutation, did not inhibit its secretion. In addition, live cells expressing $LRP5_{Wt}$ and $LRP5_{G171V}$ were biotinylated on their surfaces, and the levels of LRP5 proteins at the cell surfaces were compared by Western analysis using streptavidin-HRP after LRP5 proteins were immunoprecipitated. As shown in FIG. 2E, the amount of biotinylated $LRP5_{G171V}$ is clearly lower than that of $LRP5_{Wt}$ although the levels of two LRP5 molecules in the immunocomplexes are the same. This confirms that the G171V mutation interferes with the cell surface transport of LRP5.

The G171V mutation was predicted to be a hypermorphic allele since it is associated with bone phenotypes opposite to those exhibited by LRP5-null or hypomorphic mutations (5, 14, 25, 32). Poor cell surface presentation of $LRP5_{G171V}$ would contradict this prediction, based on the assumption that fewer receptors on the cell surface should result in a lower Wnt. However, when exogenous Wnt, which mimics a paracrine or endocrine paradigm was added, cells expressing $LRP5_{G171V}$ showed less of a response than cells expressing $LRP5_{Wt}$ (FIG. 16A). This did not occur when Wnt was coexpressed with the LRP5 molecules (FIG. 3A). The mutation does not appear to affect the activity of autocrine Wnt, suggesting that Wnt proteins may be able to bind to their receptors and activate the signaling events before the receptors are actually transported to cell surfaces. These observations explain how $LRP5_{G171V}$ gives rise to higher Wnt activity in osteoblasts during their differentiation. The mutation affects more Dkk-mediated antagonism than Wnt activity when osteoblasts produce autocrine canonical Wnts during their differentiation and there is paracrine production of Dkk1 in bone. The expression of all 19 mouse Wnt genes in bone marrow stromal osteoblast cultures was examined. One of the Wnt genes, Wnt7b, showed a marked increase in its expression after differentiation induction (FIG. 16A). The ability of Wnt 7b to stimulate the LEF-1 reporter gene, and the canonical Wnt pathway was shown (FIG. 16B). Also, Dkk1 was expressed in high levels in osteocytes and terminally differentiated osteoblasts, thus functioning as a paracrine factor for differentiating osteoblasts (FIG. 16C).

The present invention describes how the HBM G171V mutation enhances canonical Wnt signaling. The assumption that the G171V mutation may be hypermorphic was based on the phenotype associated with this mutation and a previous observation that the mutant LRP5 receptor appeared to be more resistant to Dkk-mediated inhibition of coexpressed Wnt activity (5). The initial hypothesis was that the mutation may be located in the Dkk1 binding region of LRP5 thereby interfering with the direct interaction of Dkk and LRP5. The present invention shows that the G171V mutation does not directly interfere with the interaction between LRP5 and Dkk1 at the third YWTD repeat domain of the LRP5 receptor, rather than at the first domain where the G171V mutation is located. Instead, the G171V mutation interferes with the interaction between LRP5 and its chaperon Mesd and impedes the transport of LRP5 to the cell surface, resulting in fewer LRP5 molecules on the cell surface.

The G171V mutation may still result in an increase in Wnt activity in differentiating osteoblasts provided that the differentiating osteoblasts produce autocrine Wnt proteins and have access to paracrine Dkk proteins in the bone. This is because osteoblasts expressing $LRP5_{Wt}$ or $LRP5_{G171V}$ respond to autocrine canonical Wnt similarly, but paracrine Dkk has a lower antagonistic effect on the cells expressing the mutant LRP5. This results in an increase in Wnt signaling activity in cells expressing $LRP5_{G171V}$. As shown in FIG. 16, both conditions exist: osteoblasts express a canonical Wnt, Wnt7b, and have access to Dkk1 produced from osteocytes.

Although the G171V mutation may increase bone mass through a mechanism independent of its Wnt coreceptor role, it is extremely unlikely that the G171V mutation increases bone mass by reducing Wnt activity. All available evidence, including human and mouse genetic and biochemical evidence, indicate a positive relationship between Wnt activity and osteogenesis. In both humans and mice, LRP5-null or hypomorphic mutations lead to bone phenotypes that are opposite to those exhibited by humans or mice carrying the G171V mutation (5, 14, 25, 32). In addition, the canonical Wnt proteins stimulate both proliferation and differentiation of osteoblast cells (14, 25) while Dkk1 inhibits osteoblast differentiation in a bone marrow stromal culture system. These findings, together with the one that the expression of Wnt7b is drastically upregulated after osteoblast differentiation (FIG. 16B), suggest that increases in canonical Wnt signaling activity lead to increases in bone formation. On the other hand, Dkk1 is produced at low levels in differentiating osteoblasts and at higher levels by osteocytes, the terminally differentiated osteoblasts. Dkk1 produced by osteocytes involved in the regulation of bone remodeling functions as a negative feedback mechanism in the regulation of osteoblast activity.

While the first two YWTD repeats are capable of binding Dkk1 (FIG. 15A), they are not required for DKK-mediated inhibition of Wnt signaling (FIG. 6A). This is because the binding of Dkk1 to the first two YWTD repeat domains is incompatible with the concurrent interaction of Dkk1 and Kremen as depicted in FIG. 16D. Simultaneous interactions of Dkk1 with both Kremen and LRP5/6 are required for DKK1-mediated inhibition of Wnt signaling (24). Based on the structure of the LDL receptor YWTD repeat domain, each of the first three YWTD repeat domains of LRP5 forms a barrel-like structure with a wider opening at one end and a narrower one at the other (the fourth repeat domain does not share enough amino acid sequence homology for structural deduction). This structural information allowed the identification of amino acid residues on the third YWTD repeat domain that are important for Dkk1 binding. The results showed that Dkk1 interacts with the third YWTD repeat domain via the wider opening of the barrel structure. Dkk1 interacts with the first two YWTD repeat domains in a similar manner, because simultaneous, but not individual, mutations of E721 equivalent residues in these two repeat domains (D111 and D481, respectively) abolished the binding of Dkk1-AP to R12. This E721 residue of LRP5 may form a salt bridge with a basic residue in Dkk1. This postulation is supported by a recent study on the interaction of nidogen and laminin using crystallography. The laminin interaction domain of nidogen shares amino acid sequence homology with and has the same barrel-like structure as the YWTD repeat domains of LRP5, and one of the contact residues in this nidogen domain is an E721-equivalent Glu, which forms a salt bridge with a Lys residue on laminin (47).

The present invention has identified compounds which, when provided to a cell, bind to, interact with or fit into sites or cavities found on the domains of the co-receptors involved in the stimulation, enhancement, inhibition or regulation of bone formation, or bone remodeling. These receptors include the LRP5 receptor, the LRP6 receptor, the frizzled receptor or any other receptor involved in the LRP5 or LRP6 (LRP5/6) receptor system. The frizzled receptor is a co-receptor that has a domain containing CRD, a Wnt-binding site which functions to increase or decrease Wnt activity.

The compounds were identified using screening methods described in the EXAMPLES. Some of these compounds were found to disrupt the Dkk and LRP5 interaction. Other compounds inhibited Wnt signaling by probably inhibiting the binding of Wnt to LRP5/6. The compounds of the present invention are non-native, or exogenous compounds which are not present in the cell, but originate from an outside source. They comprise agonists, which are agents that can combine with the receptors to initiate events, antagonists, which are agents that combine with the receptors to inhibit the effect of agaonists, and partial agonists, which have characteristics of both agonists and antagonists—at times appearing to cause actions and at other times inhibiting actions by decreasing the effects of agonists, for example. Some of these compounds were also found to increase affinities, or the degree to which drugs or compounds are attracted to receptor binding sites.

The $LRP5_{G171V}$ mutation which causes high bone density, attenuates the Mesd-LRP5 interaction, resulting in less LRP5 receptors present at the cell surface. Compounds were found that also disrupted the Mesd-LRP5 interaction, leading to an increase in bone density through bone formation or bone remodeling.

High amounts of Wnt activity have been associated with many cancers. Compounds were found that decreased this Wnt activity by disrupting the binding of Wnt to the second domain of the LRP5 receptor, leading to an inhibition of Wnt activity and a treatment for tumors and growths characterized by an increase in Wnt activity.

Wnt signaling has been shown to be a positive regulator of osteogenesis. Compounds were also identified which could increase Wnt activity to promote osteogenesis, bone formation or bone remodeling.

Dkk acts as a Wnt antagonist when it binds to, or interacts with, the third domain of the LRP5 receptor compounds were identified that inhibit the Dkk-LRP5 interaction to promote bone formation or remodeling. One compound, NCI366218 was tested for osteoblast differentiation in tissue culture models. Bone marrow stromal (BMS) cells were isolated from three-month old mice carrying a Green Fluorescent Protein (GFP) transgene controlled by the 2.3 Kb ColIA1 promoter (2.3Col-GFP), in which GFP was used as a marker of osteoblast cells. On the $8^{th}$ and $12^{th}$ days, the cultures were treated with the NCI366218 compound. On the same days, the cultures were treated with DMSO as a control. After the cells were treated with NCI366218, more cells became GFP positive compared to those treated with DMSO. These results indicate that the NCI366218 compound stimulates osteoblast differentiation. Compounds (such as NCI366218 and NCI8642) which attenuate Dkk-mediated inhibition of Wnt have potential therapeutic applications to treat osteoporosis and other bone diseases.

Wnt and Dkk have been shown to regulate the growth and differentiation of mesenchymal stem cells. Compounds have been identified which function as mesenchyl stem cell regulators for the regulation of bone formation and for the development and differentiation of hemaetopoietic stem cells.

Wnt has been shown to regulate the growth and differentiation of hematopoietic stem cells. Compounds have been identified which function as hemaetopoietic stem cell regulators for the regulation of bone formation and for the proliferation and expansion of stem cells in vivo and in vitro.

Materials and Methods

Cell Culture, Transfection, Preparation of CM, and Luciferase Assay.

Human embryonic kidney cell (HEK) line A293T and mouse fibroblast cell line NIH3T3 were maintained and transfected as previously described (30). Pre-osteoblast cell lines 2T3 and MC3T3 were cultured in a-MEM containing 10% FCS. For luciferase assays, cells in 24-well plates were seeded at $5 \times 10^4$ cells/well and transfected with 0.5 µg DNA/well using Lipofectamine Plus (Invitrogen, CA), as suggested by the manufacturer. The LacZ plasmid was usually used to make DNA concentrations equal for each transfection. Cell extracts were collected 24 hr after transfection. Luciferase assays were performed as previously described (30, 58). Luminescence intensity was normalized against fluorescence intensity of GFP. For the preparation of Dkk1-AP containing CM, HEK cells were seeded in 6 well-plates at $4 \times 10^5$ cells/well and transfected with 1 μg DNA/well. CMs were collected 48 hours after transfection.

Construction of Expression Plasmids and Mutagenesis.

The wild-type and mutant forms of human LRP5, LRP6, mouse Wnt1, Dkk1, and Dkk2 were generated by PCR using the high fidelity thermostable DNA polymerase Pfu Ultra (Stratagene, Calif.). HA or Flag epitope tags were introduced to the C-termini of the full-length and mutant molecules. The expression of these molecules was driven by a CMV promoter. The LEF-1 reporter gene constructs were obtained from an outside source (10).

Dkk1-AP binding assay and immunoprecipitation assay.

HEK cells in 24-well plates were transfected with LRP5 and its mutants. One day later, cells were washed with cold washing buffer (HBBS containing BSA and $NaN_3$) and incubated on ice with mouse Dkk1-AP conditioned medium for two hours. The cells were then washed three times with washing buffer and lysed. The lysates were heated at 65° C. for 10 minutes, and their AP activity was determined using a Tropix luminescence AP assay kit. The immunoprecipitation assays were carried out as previously described (30).

Biotinylation of Cell Surface Proteins.

HEK cells were transfected with LacZ, LRP5, and $LRP5_{G171V}$ expression plasmids. The cells were labeled with 0.5 mg/ml sulfo-NHS-biotin (Pierce) in ice-cold PBS, washed and lysed as previously described (19). The cell lysate was immunoprecipitated with an anti-HA antibody and A/G-agarose protein.

Primary Osteoblast Cultures.

Bone marrow stromal (BMS) osteoblast cultures from 3 month old mice were generated as previously described (23). The cells were induced to undergo osteogenic differentiation in the presence of 10 nM Dexamethasone, 8 mM β-Glycerophosphate, and 50 ug/ml ascorbic acid. The media was changed every two days.

Homology Modeling.

A homology model of the third YWTD-EGF domain of LRP5 was built with ICM (Molsoft L.L.C., La Jolla, Calif.) using sequences obtained from the Swiss-Prot/TrEMBL database (Entry Name Q9UP66 [18]). The LDL receptor (Low-Density Lipoprotein) YWTD-EGF domain (PDB code 1IJQ [22]) was chosen as the template.

Virtual Screening.

The UNITY™ program (Tripos, Inc.) was used to screen the National Cancer Institute (NCI) database for chemical compounds that were able to fit into the cavity formed by six-propellers at the end with Glu456. The candidate compounds were then docked into the Dkk 1 binding cavities of the LRP5 domains using the FlexX™ program (Tripos, Inc.) for energy minimization [17, 44]. The chemical compounds displaying the highest binding affinities in the calculations were obtained from the Drug Synthesis & Chemistry Branch, Developmental Therapeutics Program, Division of Cancer Treatment and Diagnosis, National Cancer Institute, for further experimental tests. Second and third rounds of screenings were carried out based on the results of biochemical assays.

EXAMPLES

1. Deletion Mutants of LRP5.

A set of PCR primers were designed, PCR reactions were carried out, and PCR fragments were sucloned into vectors to generate several LRP5 deletion mutants. Deletion of the third and fourth domains (residues 646 to 1198) resulted in LRP5R12; deletion of the first and second domains (residues 1 to 646) resulted in LRP5R34 and deletion of the third domain (residues 947 to 1198) resulted in LRP5R124. (see FIG. 1).

2. Domain I of LRP5 is Essential for Mesd-Mediated LRP5 Function.

2.1 The G171V Mutation in the First Domain of LRP5 Disrupts LRP5 Trafficking.

(A) Interaction of LRP5 with Mesd.

HEK cells were transfected with expression plasmids, as indicated in FIG. 2A. One day later, the cells were lysed and immunoprecipitation was carried out using an anti-Flag antibody. Mesd was Flag-tagged and all LRP5 molecules were HA-tagged. The results showed that the G171V mutation of domain I disrupted the interactions of both LRP5 with Mesd (FIG. 2A, lanes 1 and 3) and R12 with Mesd (FIG. 2B, lanes 1 and 2), whereas the E721 mutation of domain III showed no effect on the interaction (FIG. 2A, lanes 2 and 3).

(B) LRP5 Mutants do not Efficiently Present Themselves to the Cell Surface.

HEK cells were transfected with Mesd plasmids and expression plasmids, as indicated in FIG. 2B and FIG. 2C. R12TGV, R12T, R1-4 and R1-4GV (GV) are AP fusion proteins, which are LRP5 mutants lacking transmembrane domains that are secreted in the cell culture medium. One day later, the conditioned medium (CM) was collected and centrifuged at a high speed. The supernatant was either immunoprecipitated by an anti-HA antibody (FIG. 2C) or used for an AP assay (FIG. 2D). Cells were also lysed in the SDS-PAGE sample buffer and analyzed by Western blotting (lower panels of FIGS. 2C&D). The results indicate that the G171V mutation attenuates the presentation of LRP5 to the cell surface.

(C) Evaluation of Cell Surface LRP5 Levels.

HEK cells were transfected with LacZ, wildtype HA-LRP5 or HA-LRP5G171V expression plasmids. The levels of cell surface LRP5 molecules were detected by Western analysis using streptavidin-horse radish peroxidase (SA-HRP) after the cell surfaces were biotinylated and the LRP5 molecules were precipitated with anti-HA antibody (FIG. 2E upper panel). The levels of LRP5 in the immunocomplexes are shown in the lower panel. These results show a decrease in cell surface presentation of the G171V mutant.

2.2 $LRP5_{G171V}$ is Less Susceptible to Dkk1-Mediated Inhibition of the Activity of Coexpressed Wnt.

(A) Effects of the G171V Mutation on Canonical Wnt Signaling Activity.

HEK cells were transfected with plasmids, as indicated in FIG. 3A, together with LEF-1 expression plasmids, LEF-1 luciferase reporter plasmids and GFP expression plasmids. One day later, the cells were lysed. GFP levels and luciferase activity of the lysed cells were determined and normalized against GFP levels, as described in the Materials & Methods. The activity from cells transfected with LacZ was taken as 100% to establish the control. The expression of LRP5, $LRP5_{G171V}$, LRP6, and $LRP6_{G158V}$ was detected using an antibody specific to the HA tag carried by LRP5 proteins, or an anti-LRP6 antibody (FIG. 3A). The results indicate that the HBM G171V mutation did not lead to an increase in LEF-1- dependent transcriptional activity compared to wildtype (Wt) LRP5 (LRP5$_{Wt}$) by itself or in transducing signals for coexpressed Wnt.

(B) Effects of the G171V Mutation on Canonical Signaling Activity Stimulated by coexpressed Wnt1.

HEK cells were transfected with plasmids of LEF reporters, Wnt-1, Dkk1 and Kremen in the presence of LRP5$_{Wt}$ or LRP5$_{G171V}$, as indicated in FIG. 3B. Human HEK cells were transfected with LacZ, or cotransfected with Dkk1, Kremen1 and Wnt1 in the presence of LRP5 or LRP5$_{G171V}$. The protein expression level was verified by Western blotting (FIG. 3C). In the presence of both Kremen1 and DKK1, Wnt showed higher activity in HEK cells expressing LRP5$_{G171V}$ than those expressing LRP5$_{Wt}$ (FIG. 3B). These results indicate that the LRP5$_{G171V}$ tranduces more signals than the wild type in the presence of Dkk1.

2.3 Binding of Dkk1-AP to LRP5 and LRP5 Mutants.

Figure 4:
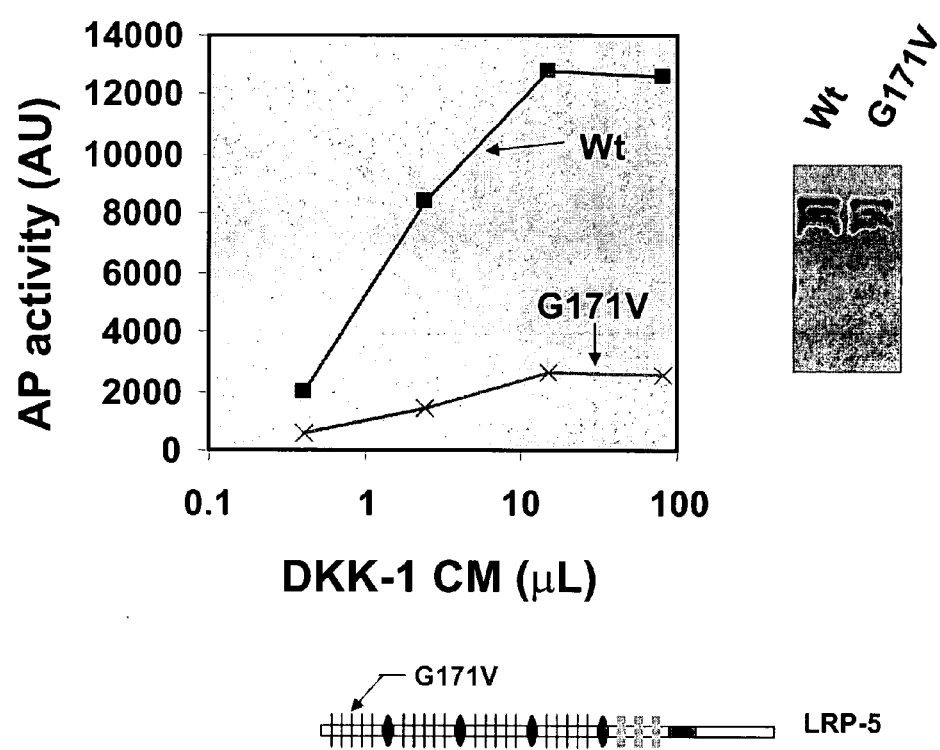
FIG. 4 illustrates that cells expressing LRP5G171 show less Dkk1 binding sites than those expressing $LRP5_{Wt}$ (FIG. 4A).

HEK cells were transfected with Mesd plasmids and LRP5 plasmids, as indicated in FIG. 4, and incubated on ice with CM prepared from HEK cells expressing Dkk1-AP. The AP activity was determined in arbitrary units (AU), as described in the Materials and Methods. The expression of Wt and mutant LRP5 molecules are shown in FIG. 4B. These results indicate that cells expressing the LRP5$_{G171V}$ mutant show less apparent Dkk binding than those expressing LRP5$_{Wt}$ (FIG. 4A), which is consistent with less LRP5$_{G171V}$ on cell surfaces, shown in FIG. 2.

3. Domain II of LRP5 is Required for Wnt Activity.

HEK cells were transfected with the LEF activity reporter plasmids and expression plasmids, as indicated in FIG. 5. Expression plasmids LRP5R494Q and LRP5G479V are LRP5 receptors with point mutations in their second domain. One day later, the cells were lysed. GFP levels and luciferase activity of the lysed cells were determined and normalized against GFP levels, as described in the Materials & Methods. FIG. 5 shows that LRP5R494Q and LRP5G479V can abolish Wnt signaling, as compared to LRP5$_{Wt}$. These results indicate that Domain II is required for Wnt activity.

4. Domain III is Required for Dkk-Mediated Inhibition.

4.1 Analysis of Domain III.

(A). Functional Analysis of Domain III.

HEK cells were transfected with the LEF activity reporter plasmids, Kremen1 plasmid and expression plasmids as indicated in the FIG. 6A. The expression of Wt LRP5 and its mutant molecules were shown in the FIG. 6B. The result shows that LRP5R12 or LRP5R124, but not LRP5R34, could still potentiate Wnt-stimulated LEF-1 activity (FIG. 6A), suggesting that LRP5R12 or LRP5R124 retains the Wnt coreceptor function. However, Dkk1 could not inhibit Wnt signaling when LRP5R12 or LRP5R124 was present (FIG. 6A). This suggests that the domain III is required for Dkk1-mediated inhibition.

(B). Binding of DKK1-AP to LRP5 and LRP5 Mutants.

HEK cells were transfected with Mesd plasmids and LRP5 plasmids, as indicated in FIG. 6C, and incubated on ice with CM prepared from HEK cells expressing Dkk1-AP. The AP activity was determined in Arbitrary Units, as described in the Methods and Materials. The expression of Wt and mutant LRP5 molecules are shown in the right panel of FIG. 6C. These results indicate that LRP5R34 contains Dkk1 binding sites, and that E721 in R34 is required for Dkk1 binding. (FIG. 6C).

4.2 Identification of the Amino Acid Residues on the Interaction Surface on Domain III which are Required for Dkk Inhibition.

(A) Schematic Representation of Ala Substitution Mutations on Interaction Surface III.

The space filled model of Domain III was deduced based on the structure of the LDL receptor YWTD repeat domain (22). The homology model of Domain III of Dkk1 was built with ICM (Molsoft L.L.C., La Jolla, Calif.) using sequences obtained from the Swiss-Prot/TrEMBL database (Entry Name Q9UP66 [18]). The Low-Density Lipoprotein (LDL) receptor YWTD-EGF domain (PDB code 1IJQ [22]) was chosen as the template. Based on the three-dimensional structure, we generated 19 LRP5 mutants containing Ala substitution mutations on the surface of Domain III (FIG. 7A). The ability of these mutant LRP5 proteins to resist Dkk1-mediated inhibition was determined and is shown in FIG. 7A. Nine of the mutants showed altered (more than 5%) sensitivity to Dkk1-mediated inhibition, and contained mutations localized on the same surface (FIG. 7A).

(B) Effect of Representative Point Mutations on the Wnt Coreceptor Activity of LRP5.

HEK cells were transfected with LEF activity reporter plasmids, Kremen1 plasmids and expression plasmids, as indicated in FIG. 7B. The expression of Wt and mutant LRP5 molecules are shown in the lower panel. Among 19 mutations, the E721 mutation showed the strongest effect on Dkk1-mediated inhibition, followed by W781, and Y719 (FIG. 7B).

5. Screening Compounds that Interact with the Specified Domains of LRP5.

5.1 Screening Compounds Using Domain III as a Template.

(A). Virtual Screening.

The UNITY™ program (Tripos, Inc.) was used to screen the National Cancer Institute (NCI) database (http://129.43.27.140/ncidb2) for chemical compounds that were able to fit into the cavity on Domain III. This database is freely searchable and includes the coordinates of 250,251 small chemical compounds. A search query was designed to consist of R764 and E721 with 0.3 Å tolerance, and a hydrophobic center with 1.0 Å tolerance that is 3.2 Å away from Trp781, pointing towards the cavity. Taking the flexibility of the compounds into consideration, the Directed Tweak algorithm in the UNITY™ program allowing for a rapid, conformationally flexible three dimensional search [21] was applied.

The candidate compounds obtained using the UNITY™ program were then docked into the Dkk1 binding surface using the FlexX™ program (Tripos, Inc.) for energy minimization [17], which quickly and flexibly docks ligands to protein-binding sites [44]. Residues E721, W864, Y719, R764, D877, F888, G782, W781 and M891, shown to be critical for Dkk1 recognition (FIG. 7A), were considered in the calculations. Following the docking procedures, the compounds were then ranked based on their predicted ability to bind to the Dkk1 binding pocket using the Cscore™ program. Cscore™ generated a relative consensus score based on how well the individual scoring functions of the protein-ligand complexes performed [8]. The Cscore™ were then subjected to final manual visual inspection. While 40 compounds with the highest consensus scores were requested from NCI, only 17 were obtained due to unavailability. These compounds were then subjected to the Dkk-1 binding assay (see section 5). Three of these compounds were found to have an effect on the binding of Dkk1 to LRP-5: NCI106164 (FIG. 8A) inhibited Dkk1 binding by 32%, while NCI39914 (FIG. 8B) and NCI660224 (FIG. 8C) stimulated Dkk1 binding by 645% and 275%, respectively. The stimulatory effect of NCI39914 and NCI660224 may be due to the enhanced interaction of these compounds with the Dkk1 binding cavity of the third domain. This enhancement could result from bridging of the gap that exists between the interaction surfaces of Dkk1 and LRP5. Since anthra-9,10-quinone (FIG. 9A) is a common substructure among compounds NCI39914 and NCI660224, anthra-9,10-quinone may play a key role in the binding interaction with LRP5. A two dimensional search for compounds found in the NCI database that are similar to anthra-9,10-quinone was performed using the similarity search algorithm of the UNITY™ program. The hits were then docked with the FlexX™ program, as previously described. 25 compounds with the highest scores were obtained from NCI and tested. Compounds NCI657566 (FIG. 9B) and NCI366218 (FIG. 10A) were able to reverse the Dkk1-mediated inhibition of Wnt signaling. A new two dimensional similarity search was conducted using a NCI366218-derived template shown in FIGS. 9C and 13 candidate compounds were identified. Biological assays (as described below) showed that NCI 8642 (FIG. 10B) was the best compound for the reversal of Dkk-mediated inhibition of Wnt signaling and the disruption of Dkk1 binding to LRP5.

(B) Biological Assays.

Biological assays were used to screen the compounds identified by virtual screening.

(I) Dkk-1 Binding Assay.

The binding of Dkk1-AP to HEK cells expressing full length LRP5 or LRP5R34 mutant lacking the first two domains was performed as described in section 2 (FIG. 4). The first batch of 17 compounds was initially screened for the inhibition of Dkk1 binding to full length LRP5. We found that NCI106164 showed a 68% inhibitory effect on Dkk1 binding, while NCI39914 and NCI660224 stimulated Dkk1 binding by approximately 654% and 276%, respectively. (see Table I.)

(II) Wnt Activity Assay.

The second and third domains of LRP5 are required for Wnt signaling, and these domains probably directly interact with Wnt molecules. Since these domains share extensive amino acid sequence homology, it is probable that certain compounds that bind to the third domain may also bind to the first two domains, potentially causing the inhibition of Wnt activity. The second batch of compounds were initially screened using the Wnt activity assay and subsequently screened using the binding assay to confirm that compounds reversing Dkk inhibition inhibited Dkk binding to LRP5. As shown in Table II, 25 compounds from the second batch were screened using the Wnt activity assay. The compounds were examined for the following: 1) basal reporter activity inhibition; 2) Wnt activity inhibition; and 3) reversal of Dkk-mediated inhibition of Wnt activity. As shown in Table II, 17 out of 25 compounds were found to inhibit Wnt activity by more than 30%. Two compounds, NCI366218 and NCI657566, were found to reverse Dkk1 mediated inhibition of Wnt signaling without affecting Wnt activity.

To determine which compounds reverse Dkk-mediated inhibition, a third batch of compounds was identified using virtual screening. 13 compounds were identified and subjected to Wnt activity screening. As shown in Table III, three compounds were found to greatly inhibit Wnt activity, and one compound (NCI8642) significantly reversed Dkk-mediated inhibition.

Both NCI8642 and NCI366218 were further characterized by Wnt activity assays and Dkk binding assays, as shown in FIG. 11 and FIG. 12. NCI8642 was more effective in the reversal of Dkk-mediated inhibition. NCI8642 also had wider range of effective concentrations than NCI366218. Both compounds began to show Wnt inhibition at high concentrations. Both compounds reversed Dkk-mediated inhibition by disrupting the interaction between Dkk1 and LRP5 since both compounds inhibited the binding of Dkk1-AP to full length LRP5 and the LRP5 R34 mutant that lacks the first two domains. NCI8642 was shown to be more effective than NCI366218 in the inhibition of Dkk1 binding, consistent with its increased effectiveness in the reversal of Dkk-mediated antagonism to Wnt signaling.

(III) Osteogenic Assay.

a) Osteogenic Assays in Culture.

Wnt stimulates the proliferation and differentiation of cultured osteoblasts and Dkk inhibits this process. Therefore, these compounds increase osteogenesis. This may be monitored by the examination of mineralization or the expression of osteogeneic markers, including the expression of BSP, osteocalcin, and collagen. The expression of GFP driven by the 2.3 Kb CollA1 promoter may also be monitored. FIG. 13 shows that NCI366218 stimulates GFP expression suggesting an increase in osteoblast differentiation. FIG. 14 shows that NCI366218 stimulates mineralization. NCI366218 also stimulates bone formation in calvarial organoculture.

b) In Vivo Osteogenic Assays

Testing for the effectiveness of these compounds in vivo may be conducted to determine if the compounds increase osteogenesis in vivo. A variety of compound doses may be injected at the outer surfaces of calvarias and into bone marrow cavities. Increased bone formation may be examined histologically and through the use of pQCT, DNX, and X-ray radioautography.

(IV) Beta-Catenin Level Assay.

Cytosolic β-catenin is stabilized by Wnt signaling. The effect of these compounds on Wnt signaling may be examined by the resulting levels of β-catenin. For example, mouse L1 cells were treated with compounds combined with Wnt3a CM, or a Dkk1-Wnt3a CM mixture for 8 hours. Cells used as a control were also treated with only Wnt3a CM, or Dkk1-Wnt3a CM mixture for 8 hours. β-catenin levels in cell lysates were measured by Western blotting or ELISA using specific anti-β-catenin antibodies. β-catenin levels from compound-treated cells were then compared to their controls. This method may also be used to screen compounds biologically.

(V) Phosphorylation of PPPSP Sites of LRP5/6

It was recently discovered that Wnt stimulates the phosphorylation of LRP5 at PPPSP motifs at the intracellular domain of LRP5 (49). Antibodies specific to phosphorylated PSPPP may be obtained and used to examine Wnt activity (49). The advantage of this assay is that it only measures receptor activation. Compounds that participate in this event are less likely to affect Wnt intracellular signaling events compared to the compounds screened using other assays. For example, HEK cells were treated with compounds combined with Wnt3a CM or DKK1-Wnt3a CM mixture for 10-60 minutes. Cells used as a control were treated with only Wnt3a CM or DKK1-Wnt3a CM mixture for 6 hours. The phosphorylation of PPPSP sites of LRP5 or LRP6 were measured by Western blotting or ELISA using specific antibodies against phosphorylated PPPSP sites. Compound treated cells were compared to their controls in order to screen compounds which showed an effect on Wnt activity according to levels of phosphorylated LDLR-PPPSP sites. This method may also be used to screen compounds biologically. [49]

5.2 Screening Compounds Using Domain II of LRP5 as a Template.

(A). Virtual Screening.

The structure of this domain may be deduced using homology modeling, as described in the "Materials and Methods". Site-directed mutagenesis may be used to map the residues that are required for Wnt signaling, as described section 4.2. Virtual screening methods may be applied to this Wnt signaling surface using the methods described in section 5.1 (A). Since domain II is involved in Wnt signaling, compounds identified using domain II as a template may increase Wnt signaling or decrease Wnt signaling. Since domain II and domain III are homologous, the compounds identified using virtual screening may: 1) increase Dkk binding; 2) decrease Dkk binding; 3) increase Dkk antagonism; and/or 4) decrease Dkk antagonism.

(B). Biological Assays.

Compounds may be tested using biological assays described in section 5.1 (B). Compounds that increase or decrease Wnt activity may be identified using methods described in section 5.1 (B), I-V. Compounds that enhance or inhibit Dkk1 binding may be determined using assays described in 5.1 (B), I. Compounds that enhance or inhibit Dkk1 antagonism may be using assays described in 5.1 (B), II.

5.3. Screening Compounds by Using Domain I of LRP5 as a Template.

(A). Virtual Screening.

The structure of this domain may be deduced using homology modeling, as described in the "Material and Methods". Site-directed mutagenesis was used to map the residues that are required for Mesd binding and function, as described in FIG. 2. Virtual screening methods were may be applied to this Mesd-binding surface using the methods described in section 5.1 (A). Since domain I is involved in Mesd functions, compound identified using domain I as a template may increase or decrease LRP5 presentation to the cell surface, thereby increasing or decreasing Wnt signaling and/or increasing or decreasing Dkk antagonism. Since domain I and domain II are homologous, the compound identified using virtual screening may increase or decrease wnt signaling. Since domain I and domain III are homologous, the compounds identified using virtual screening may: 1) increase Dkk binding; 2) decrease Dkk binding; 3) increase Dkk antagonism; and/or 4) decrease Dkk antagonism.

(B). Biological Assays.

Compounds that increase or decrease Wnt activity may be identified using methods described in section 5.1 (B), I-V. Compounds that enhance or inhibit Dkk1 bonding may be determined using assays described in section 5.1(B), I. Compounds that enhance or inhibit Dkk1 antagonism may be determined using the assays described in section 5.1 (B), II. Compounds that affect Mesd function may be determined using assays shown in FIG. 2.

6. Screening of Compounds that Interact with the CRD of the Frizzled Receptor.

Wnt signals through a transmembrane receptor of the frizzled family. This frizzled receptor passes through the cell membrane several times. A conserved cysteine-rich domain (CRD) located on the N-terminal extracellular region of frizzled acts as a Wnt binding site. Secreted frizzled-related protein Frzb-1 contains CRD and serves as an antagonist of Wnt signaling expression.

The crystal structures of the CRDs of Frizzled 8 and secreted Frizzled-related protein 3 from mice have been determined. (12) The Wnt binding sites have also been determined by Wnt-binding and mutagenesis assays.

6.1 Virtual Screening.

Virtual screening methods described in 5.1 (A) may be used to screen for potential compounds that interact with CRD to regulate the Wnt signaling pathway. A homology model may be created using the known CRD structure from mouse protein as a template. Homology models for other frizzled family members or for human frizzled protein CRD regions may be created. Based on the structure and the amino acids involved in the CRD-Wnt interaction, energy minimization methods may be used to screen to further test the biological activity of each compound. For those that show higher biological activity, a similar structural query may be used to identify additional candidate compounds.

6.2 Biological Assays.

Wnt-binding assays may be used to screen the effect of compounds on the CRD region of the frizzled proteins. CRD peptides (or frizzled proteins) expressed on the surface of the cell with detectable marker (e.g, Myc-tag). Medium containing the compound and Wnt-alkaline phosphatase fusion protein (e.g, Wnt8-AP) may be used. After incubation, binding may be determined using immuno-histochemistry staining.

Once the candidate compounds show an effect on Wnt binding, other biological assays (as described in 5.1 (B)) may be applied to determine each compounds effect on Wnt signaling. [27, 38, 12]

7. Screening of Compounds that Interact with Dkk.

7.1 Virtual screening.

The structure of Dkk1 may be solved and its interaction surfaces to Kremen and LRP5/6 may be mapped using mutagenesis, as described in section 4.2. Virtual screening may be conducted according to the methods described in section 5.1 (A). Compounds may be found to increase or decrease Dkk binding to LRP5 or Kremen, or increase or decrease Dkk-mediated inhibition of Wnt.

7.2. Biological Assays.

Compounds that increase or decrease Dkk binding to LRP5 may be determined as described in section 5.1 (B), I. Compounds that increase or decrease Dkk1 binding to Kremen may be determined as described in section 5.1 (B), I with the exception that the cells would be transfected with Kremen instead of LRP5. Compounds that increase or decrease Dkk antagonism may be as described in section 5.1 (B), II-III.

8. Screening of Compounds that Interact with Dvl Domains.

Cytoplasmic dishevelled (Dvl) proteins are activated by the Wnt-frizzled receptor complex. They are essential in both canonical and non-canonical Wnt signaling pathways. Dvl proteins are composed of an N-terminal DIX domain, a central PDZ domain, and a C-terminal DEP domain. These three conserved domains each associate with different proteins, thereby each functioning in a different pathway.

The DIX domain exists as a homodimer and forms a predominantly helical structure. This was determined using pulsed-field gradient NMR studies. The DIX domain mediates targeting to actin stress fibres and cytoplasmic vesicles in vivo. It thereby may represent a point of divergence in Wnt signaling. The stabilization of β-catenin through canonical Wnt signaling involves memberance targeting of Dvl. Lys 58, Ser 59 and Met 60 in mouse Dvl2 are critically involved in the actin interaction. Lys 68 and Glu 69 are important in cytoplasmic vesicle localization.

The PDZ domain interacts with several molecules and plays an important role in both the canonical and non-canonical Wnt pathways. The three dimensional *Xenopus* PDZ domain structure has been determined (7). Through the use of chemical-shift perturbation NMR spectroscopy and binding assays, it was shown that there is a direct interaction between the conserved motif KTXXXW of frizzled and the PDZ domain of mouse Dvl1. This allows the binding region to be determined. (57).

The DEP domain of Dvl proteins transduces signals to effector proteins downstream of Dvl in the Wnt pathway. The DEP domain of dishevelled is required for the upregulation of β-catenin activity and the stimulation of Lef-1 mediated transcription in mammalian cells. The mouse Dvl1 DEP domain's structure has been determined. (57) It has been shown that Lys434, Asp445, and Asp 448 play an important role in protein-protein interaction, and that their mutations Wnt-1 induced Lef-1 activation.

8.1 Virtual Screening.

Since the functional residues and secondary structures of the DIX domain have been determined, a screening of the existing protein domains may provide information for tertiary structural configurations potential candidates and a simulation for the same may generate candidate compounds for binding analysis. Candidate compounds affecting binding may be analyzed, and a new group of similar compounds may be assayed biologically.

Since the three dimensional structure for PDZ and DEP is known, a virtual screening method similar to the method described in section 5.1 may be used. This structure may be used as a template to create a homology model for human protein domains or other similar functional protein domains. Based on the structure and the amino acids involved in specified functions, energy minimization methods may be used to screen compounds. The biological activity of each compound may be tested. For those compounds that show high biological activity, a similar structural query may be used to find more candidate compounds, and biological activity will be further assayed.

8.2 Biological Assays.

Actin-binding inhibition assays for actin binding regions, and Xnr3 or Siamois expression levels may be used for DIX domain vesicle localization. A constructed vector containing tagged DIX may be transfected into a cell, after compound treatment. Immunofluorenscence staining may then be used to determine actin-binding inhibition. RT-PCR may be used to detect Xnr3 or Siamois levels for vesicle localization.

An in vitro binding assay may be used for initial screening for the PDZ domain. A peptide (e.g, Drp C terminal region) that binds to the PDZ domain of Dvl may be used. Purified tagged peptide bound to beads may be mixed with the PDZ domain and each compound, and after incubation, antibody may be used to detect the bound compounds. The binding efficiency effect of each compound may be determined.

To screen for compounds that will affect canonical Wnt pathway, a luciferase assay may be used for the domain. Cells may be transfected with the Dvl domain. Once these cells are incubated with compounds, Wnt/β-catenin activated luciferase activity may be assayed, thereby measuring each compound's effect.

The compounds are then classified based on their structure, and the identified compounds are further screened. Once candidate compounds affecting protein binding are identifed, other biological assays described section in 5.1(B) may be used to determine the effect of each compound on Wnt signaling. [57, 6, 58, 55, 7]

9. Screening of Compounds that Interact with β-Catenin.

β-catenin mediates the transmission of the Wnt signal into the nucleus and thereby activating the target genes. The Wnt signal prevents β-catenin degradation, allowing β-catenin to accumulate and subsequently translocate to the nucleus to form a transcriptional activating complex with members of the Tcf/LEF familiy of proteins.

The crystal structure of β-catenin, as well as the complex it forms with Axin, Lef, TCF and several other proteins, have been solved. This information may be used for the screening of compounds that regulate canonical Wnt signaling.

β-catenin contains N-terminal armadillo repeats, which are the binding sites for APC, LEF/TCF, E-cadherin and conductin/axin. All the binding sites are located in armadillo repeat units 3-8 of β-catenin. The binding of the factors occupy the groove and thus preclude the simultaneous binding of other competing β-catenin partners.

9.1 Virtual Screening

A modified strategy similar to the virtual screening described in section 5.1 may be used for identifying compounds for β-catenin interaction for binding. The homology model of β-catenin from different species may be generated using β-catenin as a template. Based on the structure and the critical amino acids involved in the interactions with LEF/TCF, Axin and APC, energy minimization methods may be used to screen for compounds to create groups of candidate compounds. Since all the aforementioned proteins occupy similar positions on β-catenin, when biological assays are used for the screening of each compound, all four interactions are tested. Based on initial biological activity, the structure of effective compounds are analyzed, and new groups of compounds are tested using similar methods. Additional biological assays may be carried out to identify the most effective compounds.

9.2 Biological assays.

Since all the β-catenin partners occupy similar positions, in vitro translation and protein binding assays may be used to determine the effectiveness of each compound. Tagged β-catenin, TCF, APC, LEF or Axin constructs may be transcribed and translated in vitro. Once they are incubated with the compounds, immunoblotting may be used to detect binding. Once compounds are identified which affect Wnt binding, other biological assays may be used, as described in section 5.1(B), to determine the effect of each compound on Wnt signaling. [52, 43, 16, 59, 11]

10. Screening of Compounds that Interact with LEF-1/TCF Transcription Factors.

Lymphoid enhancer-binding factor (LEF) is a DNA-binding protein that plays an architectural role in the assembly and function of a regulatory nucleoprotein complex. It recognizes specific nucleotide sequences through a high-mobility-group (HMG) domain. The solution structure of the HMG domain of mouse LEF-1, complexed with a 15-base-pair oligonucleotide duplex containing the optimal binding site from the TCR-alpha gene enhancer, has been solved.

10.1 Virtual Screening.

A strategy similar to the virtual screening described in section 5.1 may be used to screen for potential compounds that interact with HMG-oligonucleotide binding, to thereby affect the activity of gene expression regulation. Based on the structure, proteins containing HMG domains bend the DNA to which they bind. Any compounds that affect DNA bending or binding ability have an effect on the regulation of gene expression. The homology model for the LEF HMG domain for different species may be created using the known structure as a template. Based on the structure and the amino acids involved in HMG-oligo interaction, energy minimization methods may be used to screen for compounds. Compounds which may either force the bending or prohibit the bending are selected. The DNA biding activity used to screen the compounds. For compounds which show a much higher or much lower biological activity, a similar structural query may be used to identify additional candidate comopounds.

10.2 Biological Assays.

DNA-binding assays may be used to screen the compounds. Oligonucleotides and HMG domains are incubated with the compounds. Gel retardation assays are used to determine the DNA binding. The binding experiment may be modified with uniformly $^{13}$C labeled NMR to analyze domain bending. Since LEF controlled gene regulation is directly affected, luciferase assay may also be used for detecting compound effects. Once compounds affecting protein binding are identified, other biological assays described in 5.1(B) may be used to determine the effect of each compound on Wnt signaling. [33]

11. Screening of Compounds that Interact with any Other Wnt Signaling-Related Proteins.

Additional protein factors involved in Wnt signaling exist. Their structure may be solved in the future. Based on interaction surface structures, compounds may be screened and their biological activity tested, as described in section 5.

REFERENCES 1. 2001. NIH Consensus Conference Development Panel on Osteoporosis Prevention,
Diagnosis and Therapy. JAMA 285:785-795.
2. Babij, P., W. Zhao, C. Small, Y. Kharode, P. J. Yaworsky, M. L. Bouxsein, P. S. Reddy, P. V. Bodine, J. A. Robinson, B. Bhat, J. Marzolf, R. A. Moran, and F. Bex. 2003. High bone mass in mice expressing a mutant LRP5 gene. J Bone Miner Res 18:960-74.
3. Bafico, A., G. Liu, A. Yaniv, A. Gazit, and S. A. Aaronson. 2001. Novel mechanism of Wnt signalling inhibition mediated by Dickkopf-1 interaction with LRP6/Arrow. Nat Cell Biol 3:683-6.
4. Bain, G., T. Muller, X. Wang, and J. Papkoff. 2003. Activated beta-catenin induces osteoblast differentiation of C3H10T1/2 cells and participates in BMP2 mediated signal transduction. Biochem Biophys Res Commun 301:84-91.
5. Boyden, L. M., J. Mao, J. Belsky, L. Mitaner, A. Farhi, M. A. Mitnick, D. Wu, K. Insogna, and R. P. Lifton. 2002. High bone density due to a mutation in LDL-receptor-related protein 5. N Engl J Med 346:1513-21.
6. Capelluto D G, Kutateladze T G, Habas R, Finkielstein C V, He X, Overduin M. 2002. The DIX domain targets dishevelled to actin stress fibres and vesicular membranes. Nature 419(6908):726-9.
7. Cheyette Bn, Waxman J S, Miller J R, Takemaru K, Sheldahl L C, Khlebtsova N, Fox EP, Earnest T, Moon R T. 2002. Dapper, a Dishevelled-Associated Antagonist of beta-catenin and JNK signaling is required for notochord formation. Dev Cell, Vol 2 449-461.
8. Clark, R. D., Strizhev, A., Leonard, J. M., Blake, J. F., and Matthew, J. B. 2002. *Consensus Scoring for Ligand/Protein Interactions* J. Mol. Graph.
9. Culi, J., and R. S. Mann. 2003. Boca, an endoplasmic reticulum protein required for wingless signaling and trafficking of LDL receptor family members in Drosophila. Cell 112:343-54.
10. Dale, T. C. 1998. Signal transduction by the Wnt family of ligands. Biochem. J. 329:209-223.
11. Daniels D L, Weis W I. 2002. ICAT inhibits beta-catenin binding to Tcf/Lef-family transcription factors and the general coactivator p300 using independent structural modules. Mol Cell. 10(3):573-84.
12. Dann C E, Hsieh J C, Rattner A, Sharma D., Nathans J., Leahy D J. 2001. Insights into Wnt binding and signaling from the structures of two Frizzled cysteine-rich domain. Nature, Vol. 412, 86-90.
13. Glinka, A., W. Wu, H. Delius, A. P. Monaghan, C. Blumenstock, and C. Niehrs. 1998. Dickkopf-1 is a member of a new family of secreted proteins and functions in head induction. Nature 391:357-62.
14. Gong, Y., R. B. Slee, N. Fukai, G. Rawadi, S. Roman-Roman, A. M. Reginato, H. Wang, T. Cundy, F. H. Glorieux, D. Lev, M. Zacharin, K. Oexle, J. Marcelino, W. Suwairi, S. Heeger, G. Sabatakos, S. Apte, W. N. Adkins, J. Allgrove, M. Arslan-Kirchner, J. A. Batch, P. Beighton, G. C. Black, R. G. Boles, L. M. Boon, C. Borrone, H. G. Brunner, G. F. Carle, B. Dallapiccola, A. De Paepe, B. Floege, M. L. Halfhide, B. Hall, R. C. Hennekam, T. Hirose, A. Jans, H. Juppner, C. A. Kim, K. Keppler-Noreuil, A. Kohlschuetter, D. LaCombe, M. Lambert, E. Lemyre, T. Letteboer, L. Peltonen, R. S. Ramesar, M. Romanengo, H. Somer, E. Steichen-Gersdorf, B. Steinmann, B. Sullivan, A. Superti-Furga, W. Swoboda, M. J. van den Boogaard, W. Van Hul, M. Vikkula, M. Votruba, B. Zabel, T. Garcia, R. Baron, B. R. Olsen, and M. L. Warman. 2001. LDL receptor-related protein 5 (LRP5) affects bone accrual and eye development. Cell 107:513-23.
15. Gumbiner, B. M. 1998. Propagation and localization of Wnt signaling. Current Opinion in Genetics & Development 8:430-5.
16. Graham T A, Weaver C, Mao F, Kimelman D, Xu W. 2000. Crystal structure of a beta-catenin/Tcf complex. Cell. 103 (6):885-96.
17. Gruneberg, S., Wendt, B., and Klebe, G. 2001. Angew. Chem. Int. Ed Engl. 40, 389-393.
18. Hey P J, Twells R C, Phillips M S, Yusuke Nakagawa, Brown S D, Kawaguchi Y, Cox R, Guochun Xie, Dugan V, Hammond H, Metzker M L, Todd J A, Hess J F. 1998. Gene. 216, 103-11.
19. Hsieh, J. C., L. Lee, L. Zhang, S. Wefer, K. Brown, C. DeRossi, M. E. Wines, T. Rosenquist, and B. C. Holdener. 2003. Mesd encodes an LRP5/6 chaperone essential for specification of mouse embryonic polarity. Cell 112:355-67.
20. Hsu, S. C., J. Galceran, and R. Grosschedl. 1998. Modulation of Transcriptional Regulation By Lef-1 in Response to Wnt-1 Signaling and Association With Beta-Catenin. Molecular and Cellular Biology 18:4807-4818.
21. Hurst, T. 1994. *Directed Tweak Technique* J. Chem. Inf. Comput. Sci. 34, 190-196.
22. Jeon, H., W. Meng, J. Takagi, M. J. Eck, T. A. Springer, and S. C. Blacklow. 2001. Implications for familial hypercholesterolemia from the structure of the LDL receptor YWTD-EGF domain pair. Nat Struct Biol 8:499-504.
23. Kalajzic, I., Z. Kalajzic, M. Kaliterna, G. Gronowicz, S. H. Clark, A. C. Lichtler, and D. Rowe. 2002. Use of type I collagen green fluorescent protein transgenes to identify subpopulations of cells at different stages of the osteoblast lineage. J Bone Miner Res 17:15-25.
24. Kannus, P., M. Palvanen, S. Niemi, J. Parkkari, and M. Jarvinen. 2000. Epidemiology of osteoporotic pelvic fractures in elderly people in Finland: sharp increase in 1970-1997 and alarming projections for the new millennium. Osteoporos Int 11:443-8.

25. Kato, M., M. S. Patel, R. Levasseur, I. Lobov, B. H. Chang, D. A. Glass, 2nd, C. Hartmann, L. Li, T. H. Hwang, C. F. Brayton, R. A. Lang, G. Karsenty, and L. Chan. 2002. Cbfa1-independent decrease in osteoblast proliferation, osteopenia, and persistent embryonic eye vascularization in mice deficient in Lrp5, a Wnt coreceptor. J Cell Biol 157:303-14.

26. Krupnik, V. E., J. D. Sharp, C. Jiang, K. Robison, T. W. Chickering, L. Amaravadi, D. E. Brown, D. Guyot, G. Mays, K. Leiby, B. Chang, T. Duong, A. D. Goodearl, D. P. Gearing, S. Y. Sokol, and S. A. McCarthy. 1999. Functional and structural diversity of the human Dickkopf gene family. Gene 238:301-13.

27. Leyns L, Bouwmeester T, Kim S H, Piccolo S, De Robertis E M. 1997. Frzb-1 Is a Secreted Antagonist of Wnt Signaling Expressed in the Spemann Organizer. Cell, Vol. 88 747-756.

28. Li, L., J. Mao, L. Sun, W. Liu, and D. Wu. 2002. Second cysteine-rich domain of Dickkopf-2 activates canonical Wnt signaling pathway via LRP-6 independently of dishevelled. J Biol Chem 277:5977-81.

29. Li, L., H. Yuan, C. Weaver, J. Mao, G. H. Farr III, D. J. Sussman, J. Jonkers, D. Kimelman, and D. Wu. 1999. Axin and Frat-1 Interact with Dvl and GSK, Bridging Dvl to GSK in Wnt-Mediated Regulation of LEF-1. EMBO J 18:4233-4240.

30. Li, L., H. Yuan, W. Xie, J. Mao, E. McMahon, D. Sussman, and D. Wu. 1999. Dishevelled proteins lead to two different signaling pathways; regulation of the JNK and b-catenin pathways. J. Biol. Chem. 274:129-134.

31. Lips, P. 1997. Epidemiology and predictors of fractures associated with osteoporosis. Am J Med 103:3 S-8S; discussion 8S-11S.

32. Little, R. D., J. P. Carulli, R. G. Del Mastro, J. Dupuis, M. Osborne, C. Folz, S. P. Manning, P. M. Swain, S. C. Zhao, B. Eustace, M. M. Lappe, L. Spitzer, S. Zweier, K. Braunschweiger, Y. Benchekroun, X. Hu, R. Adair, L. Chee, M. G. FitzGerald, C. Tulig, A. Caruso, N. Tzellas, A. Bawa, B. Franklin, S. McGuire, X. Nogues, G. Gong, K. M. Allen, A. Anisowicz, A. J. Morales, P. T. Lomedico, S. M. Recker, P. Van Eerdewegh, R. R. Recker, and M. L. Johnson. 2002. A mutation in the LDL receptor-related protein 5 gene results in the autosomal dominant high-bone-mass trait. Am J Hum Genet 70:11-9.

33. Love J J, Li X, Case D A, Giese K, Grosschedl R, Wright P E. 1995. Structural basis for DNA bending by the architectural transcription factor LEF-1. Nature. 376(6543):791-5.

34. Mao, B., W. Wu, G. Davidson, J. Marhold, M. Li, B. M. Mechler, H. Delius, D. Hoppe, P. Stannek, C. Walter, A. Glinka, and C. Niehrs. 2002. Kremen proteins are Dickkopf receptors that regulate Wnt/beta-catenin signalling. Nature 417:664-7.

35. Mao, B., W. Wu, Y. Li, D. Hoppe, P. Stannek, A. Glinka, and C. Niehrs. 2001. LDL-receptor-related protein 6 is a receptor for Dickkopf proteins. Nature 411:321-5.

36. Mao, J., J. Wang, B. Liu, W. Pan, G. H. Farr, C. Flynn, H. Yuan, S. Takada, D. Kimelman, L. Li, and D. Wu. 2001. Low-density lipoprotein receptor-related protein-5 binds to axin and regulates the canonical wnt signaling pathway. Mol Cell 7:801-9.

37. Monaghan, A. P., P. Kioschis, W. Wu, A. Zuniga, D. Bock, A. Poustka, H. Delius, and C. Niehrs. 1999. Dickkopf genes are co-ordinately expressed in mesodermal lineages. Mech Dev 87:45-56.

38. Moon R T, Brown J D, Yang-Snyder J A, Miller J R. 1997. Structurally Related Receptors and Antagonists Compete for Secreted Wnt Ligands. Cell, Vol. 88, 725-728.

39. Nusse, R. 2001. Developmental biology. Making head or tail of Dickkopf. Nature 411:255-6.

40. Pandur, P., and M. Kuhl. 2001. An arrow for wingless to take-off. Bioessays 23:207-10.

41. Pfaffl, M. W. 2001. A new mathematical model for relative quantification in real-time RT-PCR. Nucleic Acids Res 29:e45.

42. Pinson, K. I., J. Brennan, S. Monkley, B. J. Avery, and W. C. Skarnes. 2000. An LDL receptor-related protein mediates Wnt singaling in mice. Nature 407:535-538.

43. Poy F, Lepourcelet M, Shivdasani R A, Eck M J. 2001. Structure of a human Tcf4-beta-catenin complex. Nat Struct Biol. 8(12):1053-7.

44. Rarey, M., Kramer, B., Lengauer, T., and Klebe, G. 1996 *A Fast Flexible Docking Method Using An Incremental Construction Algorithm* J. Mol. Biol. 261, 470-489

45. Schweizer, L., and H. Varmus. 2003. Wnt/Wingless signaling through beta-catenin requires the function of both LRP/Arrow and frizzled classes of receptors. BMC Cell Biol 4:4.

46. Semenov, M. V., K. Tamai, B. K. Brott, M. Kuhl, S. Sokol, and X. He. 2001. Head inducer Dickkopf-1 is a ligand for Wnt coreceptor LRP6. Curr Biol 11:951-61.

47. Takagi, J., Y. Yang, J. H. Liu, J. H. Wang, and T. A. Springer. 2003. Complex between nidogen and laminin fragments reveals a paradigmatic beta-propeller interface. Nature 424:969-74.

48. Tamai, K., M. Semenov, Y. Kato, R. Spokony, C. Liu, Y. Katsuyama, F. Hess, J. P. Saint-Jeannet, and X. He. 2000. LDL-receptor-related proteins in Wnt signal transduction. Nature 407:530-5.

49. Tamai K, Zeng X, Liu C, Zhang X, Harada Y, Change Z, He X. 2004. A Mechanism for Wnt Coreceptor Activation, Molecular Cell, Vol. 13, 149-156.

50. Tolwinski, N. S., M. Wehrli, A. Rives, N. Erdeniz, S. DiNardo, and E. Wieschaus. 2003. Wg/Wnt signal can be transmitted through arrow/LRP5,6 and Axin independently of Zw3/Gsk3beta activity. Dev Cell 4:407-18.

51. Van Wesenbeeck, L., E. Cleiren, J. Gram, R. K. Beals, O. Benichou, D. Scopelliti, L. Key, T. Renton, C. Bartels, Y. Gong, M. L. Warman, M. C. De Vernejoul, J. Bollerslev, and W. Van Hul. 2003. Six novel missense mutations in the LDL receptor-related protein 5 (LRP5) gene in different conditions with an increased bone density. Am J Hum Genet 72:763-71.

52. von Kries J P, Winbeck G, Asbrand C, Schwarz-Romond T, Sochnikova N, Dell'Oro A, Behrens J, Birchmeier W. 2000. Hot spots in beta-catenin for interactions with LEF-1, conductin and APC. Nat Struct Biol. 7(9):800-7.

53. Waszkowycz, B., Perkins, T. D. J., Sykes, R. A., and Li, J. 2001. *Large Scale Virtual Screening For Discovering Leads In The Post-Genomic Era* IBM Systems J. 40, 360-376.

54. Wehrli, M., S. T. Dougan, K. Caldwell, L. O'Keefe, S. Schwartz, D. Vaizel-Ohayon, E. Schejter, A. Tomlinson, and S. DiNardo. 2000. arrow encodes an LDL-receptor-related protein essential for Wingless signalling. Nature 407:527-30.

55. Wharton K A Jr. 2003 Runnin' with the Dvl: proteins that associate with Dsh/Dvl and their significance to Wnt signal transduction. Dev Biol. 253(1):1-17.

56. Wodarz, A., and R. Nusse. 1998. Mechanisms of Wnt signaling in development. Arum. Rev. Cell Dev. Biol. 14:59-88.

57. Wong H C, Bourdelas A, Krauss A, Lee H J, Shao Y, Wu D, Mlodzik M, Shi Dl, Zheng J. 2003. Direct binding of the PDZ domain of Dishevelled to a conserved internal sequence in the C-terminal region of Frizzled. Mol Cell. 12(5):1251-60.
58. Wong H C, Mao J, Nguyen J T, Srinivas S, Zhang W, Liu B, Li L, Wu D, Zheng J. 2000 Structural basis of the recognition of the dishevelled DEP domain in the Wnt signaling pathway. Nat Struct Biol. 7(12):1178-84. Yuan, H., J. Mao, L. Li, and D. Wu.
1999. Regulation of GSK and LEF-1 by Wnt, Frat and Akt; Suppression of GSK Kinase Activity is not Sufficient for LEF-1 Activation. J. Biol. Chem. 274:30419-30423.
59. Xing Y, Clements W K, Kernelman D, Xu W. 2003. Crystal structure of a beta-catenin/axin complex suggests a mechanism for the beta-catenin destruction complex. Genes Dev. 2003 Nov. 15; 17(22):2753-64.
60. Zuckerman, J. D. 1996. Hip fracture. N Engl J Med 334:1519-25.

TABLE I

Effects of chemical compounds (2 mg/ml) on Dkk1 binding

| Compound 1000 ul DMSO | | Binding Inhibitory Rate of Dkk1 % LRP5 WT |
|---|---|---|
| DMSO | 1:100 | 100 |
| 270071 | IC1 | 97 |
| 45123 | IC2 | 117 |
| 37815 | IC3 | 85 |
| 382917 | IC4 | 108 |
| 660224 | IC5 | 276 |
| 38290 | IC6 | 101 |
| 649827 | IC7 | 88 |
| 70694 | IC8 | 180 |
| 648597 | IC9 | 79 |
| 618567 | IC10 | 96 |
| 657726 | IC11 | 90 |
| 12156 | IC12 | 127 |
| 39914 | IC13 | 654 |
| 106164 | IC14 | 68 |
| 16221 | IC15 | 73 |
| 651656 | IC16 | 96 |
| 67653 | IC17 | 107 |

TABLE III

Wnt activity assay screening of Batch III

| Compound | Basal | Wnt | Wnt + Dkk |
|---|---|---|---|
| Control | 100 | 1000 | 240 |
| 37089 | 102 | 1090 | 230 |
| 97309 | 90 | 430 | 105 |
| 8642 | 101 | 1220 | 1020 |
| 66425 | 85 | 1010 | 250 |
| 113914 | 92 | 1180 | 360 |
| 364163 | 0 | 0 | 0 |
| 115934 | 88 | 800 | 190 |
| 110317 | 90 | 1110 | 250 |
| 3751 | 97 | 1090 | 304 |
| 28627 | 107 | 800 | 403 |
| 10573 | 87 | 710 | 245 |
| 620055 | 10 | 1 | 6 |
| 37179 | 92 | 960 | 240 |

TABLE II

Wnt activity assay screening of Batch II

| Compound | Basal | Wnt | Wnt + Dkk |
|---|---|---|---|
| Control | 100 | 1000 | 100 |
| 127133 | 97 | 170 | 106 |
| 1743 | 113 | 670 | 229 |
| 39963 | 115 | 970 | 114 |
| 337836 | 116 | 870 | 81 |
| 37608 | 26 | 0 | 10 |
| 372294 | 95 | 0 | 13 |
| 123823 | 79 | 220 | 137 |
| 366218 | 117 | 1220 | 476 |
| 342051 | 107 | 50 | 152 |
| 39957 | 103 | 40 | 16 |
| 4997 | 114 | 990 | 113 |
| 116405 | 88 | 230 | 23 |
| 641424 | 111 | 190 | 19 |
| 373532 | 99 | 110 | 27 |
| 25869 | 105 | 880 | 176 |
| 310659 | 128 | 130 | 21 |
| 28561 | 90 | 630 | 110 |
| 51530 | 130 | 0 | 0 |
| 128436 | 166 | 0 | 0 |
| 209942 | 100 | 750 | 136 |
| 366105 | 107 | 100 | 0 |
| 159858 | 121 | 80 | 147 |
| 106164 | 88 | 350 | 64 |
| 647082 | 95 | 940 | 105 |
| 657566 | 105 | 1140 | 227 |

Table II & Table III
NIH3T3 cells were transfected with Wnt activity luciferase reporter gene. The next day, the compounds were dissolved in DMSO at 2 mg/ml and diluted at 20 ug/ml into tissue culture medium (Basal), medium containing Wnt3a (Wnt) or medium containing both Wnt3a and Dkk1 (Wnt + Dkk). DMSO without any compound served as the control. Six hours later, the cells were lysed and Wnt activity was determined using a luciferase assay. The data shown is percent basal activity. Compounds that show more than a 100% reversal of Dkk inhibition without affecting Wnt activity are shown in red.

The invention claimed is:

1. A method for stimulating or enhancing bone formation or bone remodeling comprising administering at least one compound that binds to or interacts with at least one YWTD domain on the LRP5 or LRP6 receptor, wherein said compound disrupts the binding or interaction of Dkk1 with said YWTD domain and increases Wnt activity as determined by a biological assay, wherein said compound is selected from NCI366218, NCI8642, and NCI657566.

2. The method of claim 1, wherein a bone fracture, bone disease, bone injury, or bone abnormality is treated.

3. The method of claim 1, wherein said administering comprises inhalation, oral, intravenous, intraperitoneal, intramuscular, parenteral, transdermal, intravaginal, intranasal, mucosal, sublingual, topical, rectal, or subcutaneous administration, or any combination thereof.

* * * * *